(12) United States Patent
Strommer et al.

(10) Patent No.: US 8,442,618 B2
(45) Date of Patent: May 14, 2013

(54) METHOD AND SYSTEM FOR DELIVERING A MEDICAL DEVICE TO A SELECTED POSITION WITHIN A LUMEN

(75) Inventors: Gera Strommer, Haifa (IL); Uzi Eichler, Haifa (IL)

(73) Assignee: MediGuide Ltd., Haifa (IL)

( * ) Notice: Subject to any disclaimer, the term of this patent is extended or adjusted under 35 U.S.C. 154(b) by 2674 days.

(21) Appl. No.: 11/233,420

(22) Filed: Sep. 16, 2005

(65) Prior Publication Data

US 2006/0058647 A1 Mar. 16, 2006

Related U.S. Application Data

(63) Continuation-in-part of application No. 10/986,567, filed on Nov. 10, 2004, which is a continuation-in-part of application No. 10/938,395, filed on Sep. 9, 2004, now Pat. No. 7,778,688, which is a continuation-in-part of application No. 09/949,160, filed on Sep. 7, 2001, now Pat. No. 7,343,195, which is a continuation-in-part of application No. 09/782,528, filed on Feb. 13, 2001, now Pat. No. 7,386,339, which is a continuation-in-part of application No. 09/314,474, filed on May 18, 1999, now Pat. No. 6,233,476.

(51) Int. Cl.
*A61B 5/05* (2006.01)
(52) U.S. Cl.
USPC ............................ 600/424; 600/426; 600/427
(58) Field of Classification Search .................. 600/424, 600/426, 427
See application file for complete search history.

(56) References Cited

U.S. PATENT DOCUMENTS

| | | | |
|---|---|---|---|
| 3,937,066 | A | 2/1976 | Green et al. |
| 3,974,826 | A | 8/1976 | Eggleton et al. |
| 3,990,296 | A | 11/1976 | Erikson |
| 4,398,540 | A | 8/1983 | Takemura et al. |

(Continued)

FOREIGN PATENT DOCUMENTS

| | | |
|---|---|---|
| EP | 0894473 | 2/1999 |
| EP | 1 088 515 A1 | 4/2001 |

(Continued)

OTHER PUBLICATIONS

Panza, Julio A., "Real-time three-dimensional echocardiography: An overview", *The International Journal of Cardiovascular Imaging* 17:227-235, 2001.

*Primary Examiner* — Brian Casler
*Assistant Examiner* — Joseph M Santos
(74) *Attorney, Agent, or Firm* — Dykema Gossett PLLC

(57) ABSTRACT

A system and method are provided for delivering a medical device on a catheter to a selected position within a lumen of the body. A medical positioning system (MPS) acquires MPS data for points within the lumen using an MPS sensor on the catheter. Each of the points is associated with a three-dimensional coordinate system and an activity state of an organ of the patient. A user interface receives position data for the selected position. The position date is associated with an MPS representation associated with one of the points. A processor determines a plurality of temporal three-dimensional trajectory representations based on the MPS data and corresponding to the respective activity states of the organ. The processor superimposes the temporal three-dimensional trajectory representations on a two-dimensional image according to the activity states of the organ thereby enabling an operator to visually navigate the medical device toward the selected position.

47 Claims, 23 Drawing Sheets

U.S. PATENT DOCUMENTS

| | | | |
|---|---|---|---|
| 4,737,794 A | 4/1988 | Jones | |
| 5,016,642 A | 5/1991 | Dukes et al. | |
| 5,152,290 A | 10/1992 | Freeland | |
| 5,159,931 A | 11/1992 | Pini | |
| 5,318,025 A | 6/1994 | Dumoulin et al. | |
| 5,360,008 A | 11/1994 | Campbell | |
| 5,398,691 A | 3/1995 | Martin et al. | |
| 5,445,150 A | 8/1995 | Dumoulin et al. | |
| 5,453,686 A | 9/1995 | Anderson | |
| 5,529,070 A | 6/1996 | Augustine et al. | |
| 5,577,502 A | 11/1996 | Darrow et al. | |
| 5,588,432 A | 12/1996 | Crowley | |
| 5,622,174 A | 4/1997 | Yamazaki | |
| 5,646,525 A | 7/1997 | Gilboa et al. | |
| 5,669,385 A | 9/1997 | Pesque et al. | |
| 5,690,113 A | 11/1997 | Sliwa, Jr. et al. | |
| 5,724,982 A | 3/1998 | Schnurer et al. | |
| 5,730,129 A | 3/1998 | Darrow et al. | |
| 5,740,808 A * | 4/1998 | Panescu et al. | 600/424 |
| 5,744,953 A | 4/1998 | Hansen | |
| 5,787,889 A | 8/1998 | Edwards et al. | |
| 5,806,521 A | 9/1998 | Morimoto et al. | |
| 5,810,008 A | 9/1998 | Dekel et al. | |
| 5,830,145 A | 11/1998 | Tenhoff | |
| 5,830,222 A | 11/1998 | Makower | |
| 5,846,200 A | 12/1998 | Schwartz | |
| 5,899,860 A | 5/1999 | Pfeiffer et al. | |
| 5,906,578 A | 5/1999 | Rajan et al. | |
| 5,913,820 A | 6/1999 | Bladen et al. | |
| 5,924,989 A | 7/1999 | Polz | |
| 5,928,248 A | 7/1999 | Acker | |
| 5,935,075 A | 8/1999 | Casscells | |
| 5,938,606 A | 8/1999 | Bonnefous et al. | |
| 5,949,491 A | 9/1999 | Callahan et al. | |
| 5,955,879 A | 9/1999 | Durdle et al. | |
| 5,957,844 A | 9/1999 | Dekel et al. | |
| 5,967,980 A | 10/1999 | Ferre et al. | |
| 5,976,088 A | 11/1999 | Urbano et al. | |
| 5,993,390 A | 11/1999 | Savord et al. | |
| 5,994,690 A | 11/1999 | Kulkarni et al. | |
| 6,006,126 A | 12/1999 | Cosman | |
| 6,030,343 A | 2/2000 | Chechersky et al. | |
| 6,035,856 A | 3/2000 | LaFontaine et al. | |
| 6,047,080 A | 4/2000 | Chen et al. | |
| 6,134,003 A | 10/2000 | Tearney et al. | |
| 6,148,095 A | 11/2000 | Prause et al. | |
| 6,169,917 B1 | 1/2001 | Masotti et al. | |
| 6,175,669 B1 | 1/2001 | Colston et al. | |
| 6,216,029 B1 | 4/2001 | Paltieli | |
| 6,228,028 B1 | 5/2001 | Klein et al. | |
| 6,233,476 B1 | 5/2001 | Strommer et al. | |
| 6,246,898 B1 | 6/2001 | Vesely et al. | |
| 6,275,724 B1 * | 8/2001 | Dickinson et al. | 600/424 |
| 6,317,621 B1 | 11/2001 | Graumann et al. | |
| 6,321,109 B2 | 11/2001 | Ben-Haim et al. | |
| 6,381,350 B1 | 4/2002 | Klingensmith et al. | |
| 6,385,476 B1 | 5/2002 | Osadchy et al. | |
| 6,390,982 B1 | 5/2002 | Bova et al. | |
| 6,405,072 B1 | 6/2002 | Cosman | |
| 6,416,476 B1 | 7/2002 | Ogasawara et al. | |
| 6,432,041 B1 | 8/2002 | Taniguchi et al. | |
| 6,470,207 B1 * | 10/2002 | Simon et al. | 600/426 |
| 6,498,944 B1 | 12/2002 | Ben-Haim et al. | |
| 6,501,981 B1 * | 12/2002 | Schweikard et al. | 600/427 |
| 6,546,271 B1 | 4/2003 | Reisfeld | |
| 6,556,695 B1 | 4/2003 | Packer et al. | |
| 6,589,163 B2 | 7/2003 | Aizawa et al. | |
| 6,626,902 B1 | 9/2003 | Kucharczyk et al. | |
| 6,733,458 B1 | 5/2004 | Steins et al. | |
| 6,773,393 B1 | 8/2004 | Taniguchi et al. | |
| 6,775,404 B1 | 8/2004 | Pagoulatos et al. | |
| 6,788,967 B2 | 9/2004 | Ben-Haim et al. | |
| 6,895,267 B2 | 5/2005 | Panescu et al. | |
| 7,007,699 B2 | 3/2006 | Martinelli et al. | |
| 7,195,587 B2 | 3/2007 | Taniguchi et al. | |
| 7,197,354 B2 | 3/2007 | Sobe | |
| 7,235,084 B2 | 6/2007 | Skakoon et al. | |
| 7,263,397 B2 | 8/2007 | Hauck et al. | |
| 7,343,195 B2 | 3/2008 | Strommer et al. | |
| 7,386,339 B2 | 6/2008 | Strommer et al. | |
| 7,398,116 B2 | 7/2008 | Edwards | |
| 7,778,688 B2 | 8/2010 | Strommer | |
| 2001/0031919 A1 | 10/2001 | Strommer et al. | |
| 2001/0044578 A1 * | 11/2001 | Ben-Haim et al. | 600/424 |
| 2002/0007124 A1 | 1/2002 | Woodward | |
| 2002/0049375 A1 | 4/2002 | Strommer et al. | |
| 2002/0193686 A1 | 12/2002 | Gilboa | |
| 2003/0074011 A1 | 4/2003 | Gilboa et al. | |
| 2004/0034297 A1 | 2/2004 | Darrow et al. | |
| 2004/0097804 A1 | 5/2004 | Sobe | |
| 2004/0116775 A1 | 6/2004 | Taniguchi et al. | |
| 2004/0138548 A1 | 7/2004 | Strommer et al. | |
| 2004/0215071 A1 | 10/2004 | Frank et al. | |
| 2005/0033149 A1 | 2/2005 | Strommer et al. | |
| 2005/0049493 A1 | 3/2005 | Kerby et al. | |
| 2005/0107688 A1 | 5/2005 | Strommer et al. | |
| 2005/0197557 A1 | 9/2005 | Strommer et al. | |
| 2006/0058647 A1 | 3/2006 | Strommer et al. | |
| 2006/0064006 A1 | 3/2006 | Strommer et al. | |
| 2006/0079745 A1 | 4/2006 | Viswanathan | |
| 2007/0287901 A1 | 12/2007 | Strommer et al. | |
| 2008/0175463 A1 | 7/2008 | Strommer et al. | |
| 2009/0182224 A1 | 7/2009 | Shmarak et al. | |
| 2010/0331950 A1 | 12/2010 | Strommer | |

FOREIGN PATENT DOCUMENTS

| | | |
|---|---|---|
| JP | 62032304 | 2/1987 |
| JP | 8500441 | 1/1996 |
| JP | 11110114 | 5/1999 |
| JP | 2001170027 | 6/2001 |
| JP | 2002200058 | 7/2002 |
| JP | 2007502187 | 2/2007 |
| WO | WO-94/04938 | 3/1994 |
| WO | WO-96/05768 | 2/1996 |
| WO | WO-96/41119 | 12/1996 |
| WO | 97/29682 | 8/1997 |
| WO | WO-97/029685 | 8/1997 |
| WO | WO-97/36143 | 10/1997 |
| WO | 99/43253 | 9/1999 |
| WO | 00/10456 | 3/2000 |
| WO | 00/16684 | 3/2000 |
| WO | 02/064011 A2 | 8/2002 |
| WO | WO-03/059167 | 7/2003 |
| WO | WO-2004/060157 | 7/2004 |
| WO | WO-2004/062501 | 7/2004 |
| WO | WO-2005/039391 | 5/2005 |

* cited by examiner

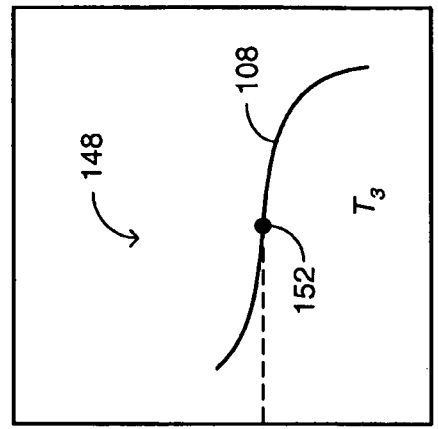
FIG. 4C
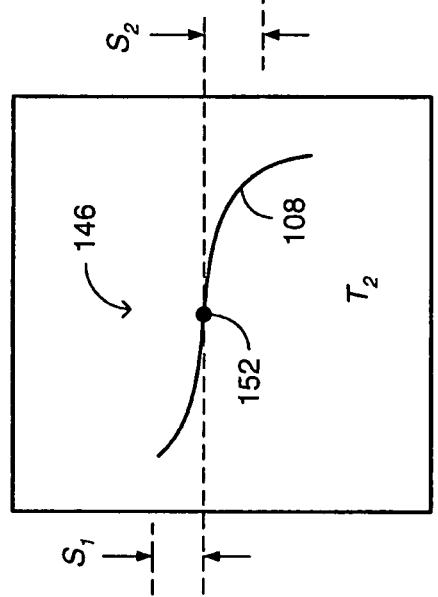
FIG. 4B
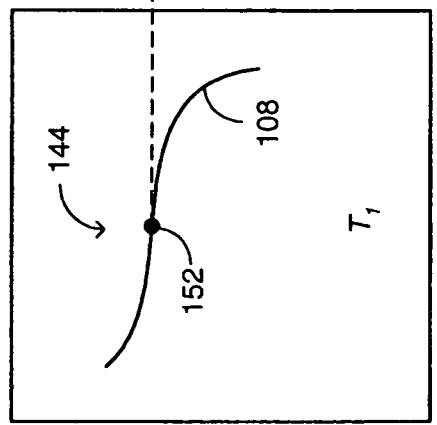
FIG. 4A
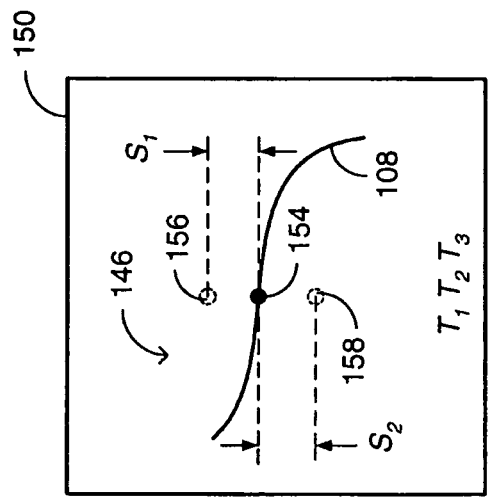
FIG. 4D
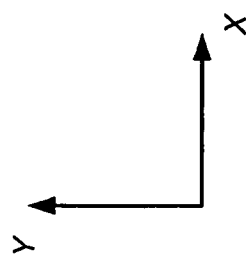

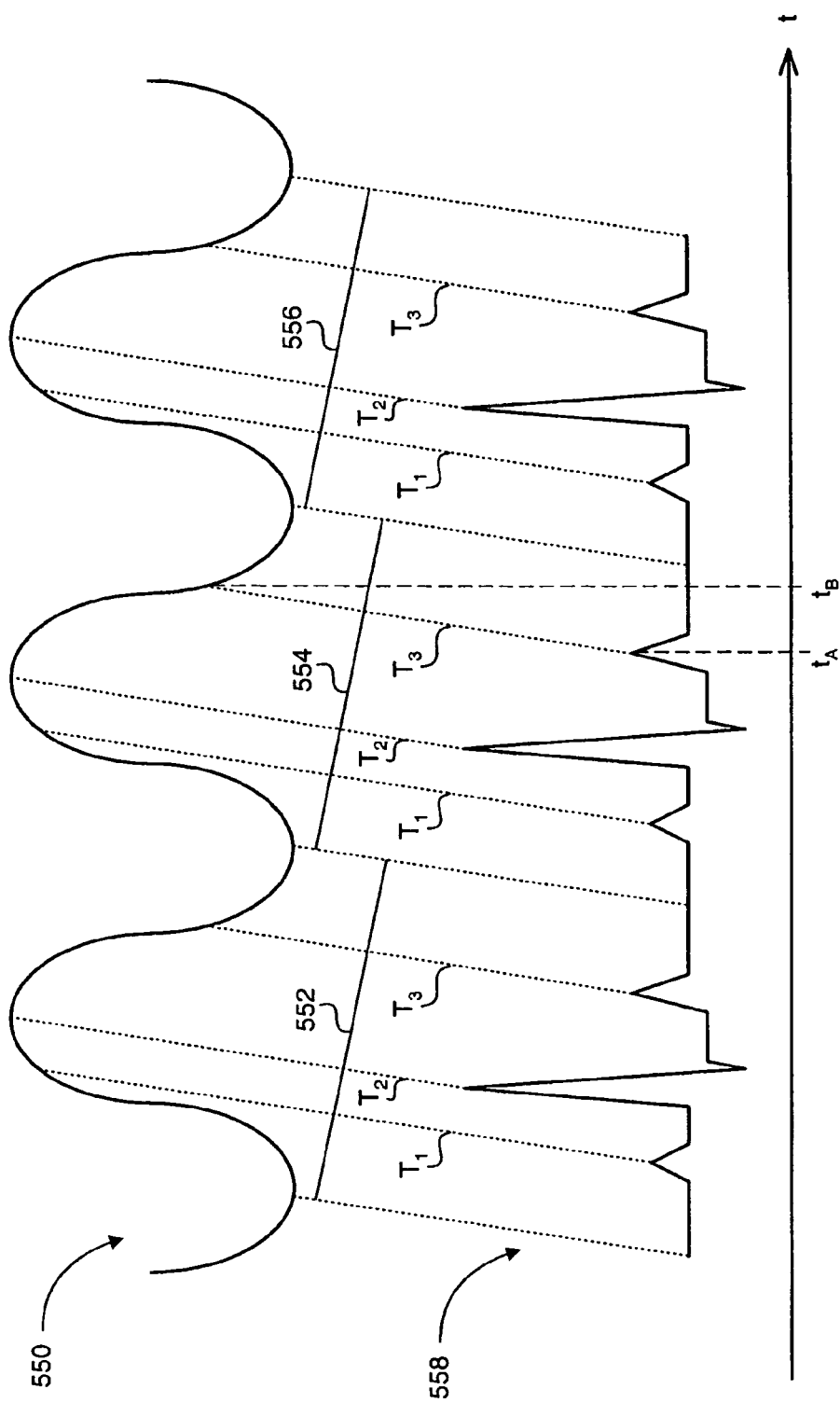

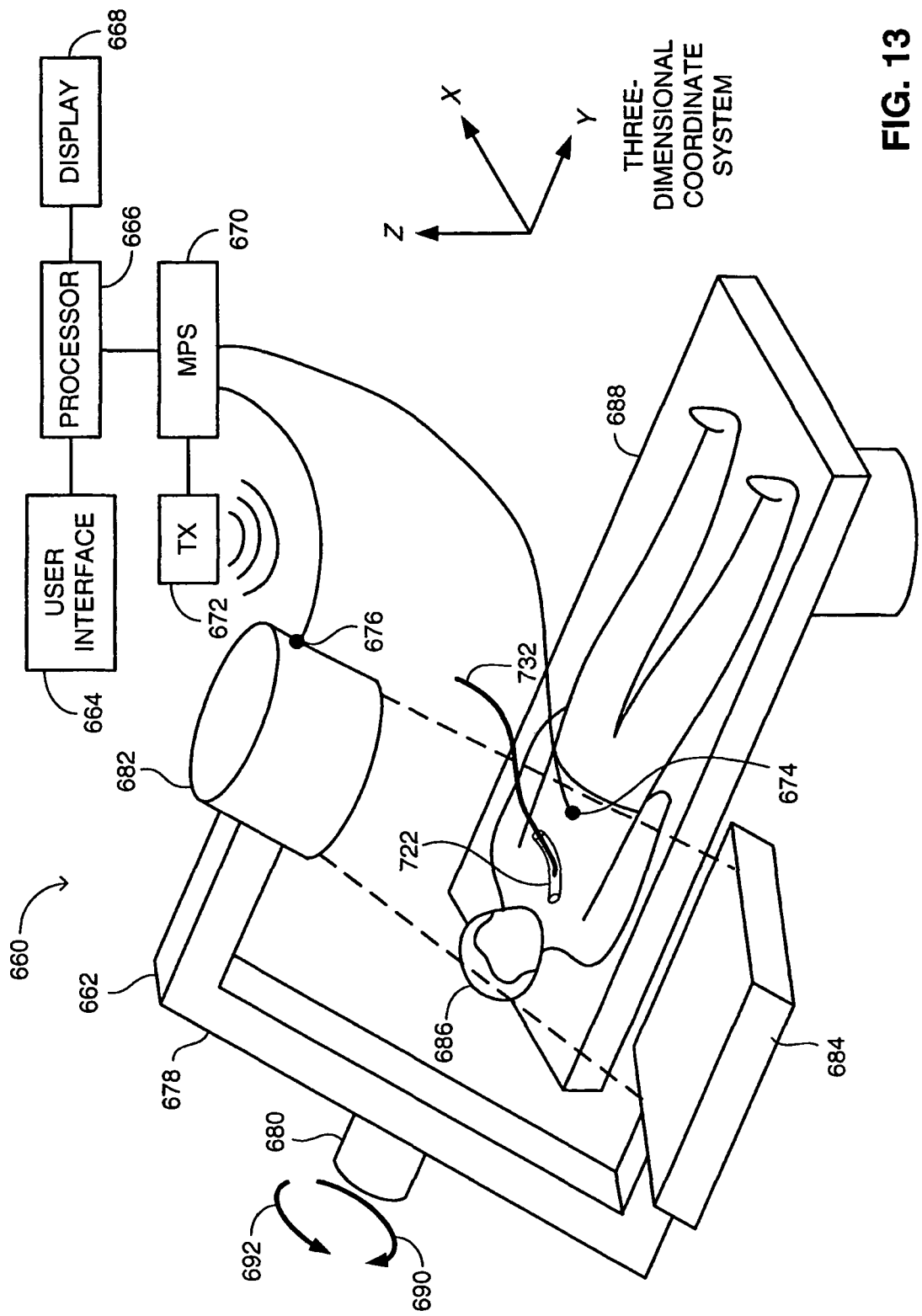

METHOD AND SYSTEM FOR DELIVERING A MEDICAL DEVICE TO A SELECTED POSITION WITHIN A LUMEN

This application is a continuation in part application of U.S. application Ser. No. 10/986,567 filed Nov. 10, 2004, the entire disclosure of which is incorporated herein by reference, which is a continuation in part application of U.S. application Ser. No. 10/938,395, now U.S. Pat. No. 7,778,688, filed Sep. 9, 2004, the entire disclosure of which is incorporated herein by reference, which is a continuation in part application of U.S. application Ser. No. 09/949,160, now U.S. Pat. No. 7,343,195, filed Sep. 7, 2001, the entire disclosure of which is incorporated herein by reference, which is a continuation in part application of U.S. application Ser. No. 09/782,528, now U.S. Pat. No. 7,386,339 filed Feb. 13, 2001, the entire disclosure of which is incorporated herein by reference, which is a continuation in part application of U.S. application Ser. No. 09/314,474, now U.S. Pat. No. 6,233,476, filed May 18, 1999, the entire disclosure of which is incorporated herein by reference.

FIELD OF THE DISCLOSED TECHNIQUE

The disclosed technique relates to medical operations in general, and to methods and systems for mounting a stent in the body of a patient, in particular.

BACKGROUND OF THE DISCLOSED TECHNIQUE

An occluded vessel in the body of a patient is cleared by severing the occluding matter (e.g., the intima of a blood vessel), for example by inflating a balloon (i.e., angioplasty). This severing action initiates a healing process in the vessel, which causes production of new tissue cells, thereby once again constricting the passage through the vessel. The growth of tissue cells occurs over a period of a few months following the surgery. In order to keep the passageway open for a longer period of time, and prevent tissue cell to grow as a result of healing, a rigid thin wall tube whose wall is in form of wire mesh (i.e., stent) is mounted in the severed portion of the vessel, within the vessel.

Methods and systems for maneuvering the stent catheter to the desired location within the vessel, after severing the vessel are known in art. For example, a set of radio-opaque marker bands are attached to the catheter close to the stent, thereby enabling the physician to navigate the catheter by viewing the marker band in a real-time X-ray image of the vessel. In another case, the physician can view a representation of the position and orientation of the stent on the real-time X-ray image, according to position and orientation data acquired by a medical positioning system (MPS) sensor, attached to the catheter close to the stent.

U.S. Pat. No. 5,928,248 issued to Acker and entitled "Guided Deployment of Stents", is directed to an apparatus for applying a stent in a tubular structure of a patient. The apparatus includes a catheter, a hub, a pressure control device, a balloon, a stent, a probe field transducer, a plurality of external field transducers, a field transmitting and receiving device, a computer, an input device and a cathode ray tube. The catheter includes a bore. The hub is affixed to a proximal end of the catheter. The balloon is mounted on a distal end of the catheter. The pressure control device is connected to the balloon through the hub and the bore. The stent is made of a shape memory alloy and is located on the balloon.

The probe field transducer is located within the catheter, at a distal end thereof. The external field transducers are located outside of the patient (e.g., connected to the patient-supporting bed). The field transmitting and receiving device is connected to the external field transducers, the probe field transducer and to the computer. The computer is connected to the cathode ray tube and to the input device.

A user calibrates the field transmitting and receiving device in an external field of reference, by employing the external field transducers. The field transmitting and receiving device together with the computer, determine the position and orientation of the probe field transducer in the external field of reference. The user views the position and orientation of a representation of the stent which is located within a tubular structure of the patient, on the cathode ray tube. When the user determines that the distal end is located at the desired location within the tubular structure, the user expands the stent by operating the pressure control device and inflating the balloon, thereby positioning the stent at the desired location.

U.S. Pat. No. 5,830,222 issued to Makower and entitled "Device, System and Method for Interstitial Transvascular Intervention", is directed to a method for gaining percutaneous access to a diseased vessel through an adjacent intact vessel. Using this method, it is possible to bypass the diseased vessel, such as a coronary artery, through the intact vessel, such as a cardiac vein. The diseased vessel may include an occlusion that restricts the flow. A guide-catheter is advanced through the vena cava into the coronary sinus, within the right atrium of the heart. A transvascular interstitial surgery (TVIS) guide catheter is inserted through the guide-catheter and advanced through the cardiac vein over a first guidewire, to a desired location adjacent the coronary artery.

The TVIS guide-catheter includes a balloon, a TVIS probe and either or both of active orientation detection means and passive orientation detection means. The TVIS probe is a rigid wire, antenna, light guide or energy guide capable of being inserted in tissue. The passive orientation detection means allow radiographic, fluoroscopic, magnetic or sonographic detection of position and orientation of the TVIS probe. The active orientation detection means is a transmitter. A second guidewire is inserted into the coronary artery adjacent the cardiac vein, wherein the second guidewire includes a small receiver to receive a signal emitted by the active orientation detection means. The second guidewire further includes a wire bundle which is capable to return the signal detected by the receiver, to an operator, thereby enabling the operator to determine the position and location of the TVIS probe.

When the orientation of the TVIS guide-catheter is assured, the balloon is inflated against the wall of the cardiac vein, in order to block the flow, stabilize the TVIS guide-catheter within the cardiac vein and dilate the passageway. The TVIS probe, is then advanced through the wall of the cardiac vein into the coronary artery, thereby bypassing the diseased section of the coronary artery.

U.S. patent Publication No. 20020049375 entitled "Method and Apparatus for Real Time Quantitative Three-Dimensional Image Reconstruction of a Moving Organ and Intra-Body Navigation", is directed to a system for displaying an image of a lumen of a patient into which a surgical catheter is inserted, while taking into account the movements of the lumen caused by the heart beats of the patient. The system includes the surgical catheter, an imaging catheter, an imaging system, a medical positioning system (MPS), a transmitter, a body MPS sensor, a processor, a plurality of electrocardiogram (ECG) electrodes, an ECG monitor, a database, and a display. The surgical catheter includes a catheter MPS sensor located at a tip thereof. The imaging catheter includes an imaging MPS sensor and an image detector, both located at a tip of the imaging catheter.

The ECG electrodes are attached to the body of the patient and to the ECG monitor. The body MPS sensor is attached to the body of the patient and to the MPS. The processor is coupled with the imaging system, the MPS, the ECG monitor, the database and with the display. The MPS is coupled with the transmitter. During the scanning procedure the MPS is coupled with the imaging MPS sensor. During the surgical procedure the MPS is coupled with the catheter MPS sensor. The imaging system is coupled with the image detector. The imaging MPS sensor and the catheter MPS sensor send a signal respective of the position and orientation of the tip of the imaging catheter and the surgical catheter, respectively, to the MPS.

During the scanning procedure, an operator inserts the imaging catheter into the lumen and advances it therein, while the image detector scans the inner wall of the lumen and transmits detected two-dimensional images to the imaging system. The processor reconstructs a plurality of three-dimensional images according to the two-dimensional images and according to the coordinates of the tip of the imaging catheter determined by the MPS, while the processor associates each three-dimensional image with a respective activity state of the heart of the patient.

During the surgical procedure, the operator inserts the surgical catheter into the lumen and the catheter MPS sensor sends a location signal respective of the position and orientation of the tip of the surgical catheter to the MPS. As the operator moves the surgical catheter within the lumen, the processor determines a sequence of three-dimensional images of the lumen by retrieving data from the database, and according to the current position and orientation of the tip of the surgical catheter and the current activity state of the heart of the patient. The display displays the three-dimensional images in sequence, according to a video signal received from the processor.

U.S. Pat. No. 6,035,856 issued to LaFontaine et al., and entitled "Percutaneous Bypass with Branching Vessel", is directed to a method for performing a bypass on a first occlusion of a branching vessel of the aorta. A coronary artery which includes the first occlusion, and a branching vessel branch out of the aorta. A standard guide-catheter is advanced through the aorta up to the ostium of the branching vessel. An occlusion forming device is advanced through the guide-catheter into the branching vessel, to produce a second occlusion in the branching vessel. The occlusion device includes an elongate portion and a heated balloon.

The occlusion forming device is removed from the aorta through the guide-catheter and a cutting device is advanced through the guide-catheter proximal to the second occlusion. The cutting device includes an elongate member, a steerable guidewire, a proximal occlusion balloon, a distal balloon, a stent, a cutting blade, a first piece of magnetic material and a transmitter. The cutting blade is located distal to the distal balloon, the first piece of the magnetic material is located between the cutting blade and the distal balloon and the transmitter is located within the distal balloon. The distal balloon is located within the stent. The transmitter emits radio frequency signals.

The wall of the branching vessel is cut by employing the cutting blade. The distal balloon is kept in the expanded position, in order to occlude the branching vessel after the branching vessel has been cut. The severed end of the branching vessel is steered toward a region of the coronary artery distal to the first occlusion, by maneuvering the steerable guidewire or by manipulating the first piece of the magnetic material by a second piece of magnetic material, wherein the second piece of magnetic material is located outside the body of the patient.

The true position and the relative position of the transmitter and thus the position of the severed end of the branching vessel, is determined by employing a triangulation and coordinate mapping system. The triangulation and coordinate mapping system includes three reference electrodes which are located outside the body of the patient. Two of the reference electrodes are located on opposite sides of the heart and the third is located on the back. The three reference electrodes are used to triangulate on the transmitter.

When the severed end of the branching vessel is properly positioned, an aperture is formed in the coronary artery distal to the first occlusion, by employing the cutting blade. The severed end of the branching vessel is inserted into the coronary artery through the aperture and the stent is expanded by inflating the distal balloon, thereby attaching the severed end of the branching vessel to the lumen of the coronary artery.

U.S. Pat. No. 6,385,476 B1 issued to Osadchy et al., and entitled "Method and Apparatus for Intracardially Surveying a Condition of a Chamber of a Heart", is directed to a method for navigating a catheter within the heart of a patient, in order to acquire condition information of a chamber of the heart. A contrast agent is injected into the heart and a first image (i.e., a contrast assisted fluoroscopy image) of the left ventricle is acquired. The catheter is advanced into the heart chamber, and a second image of the chamber showing the catheter contained therein is acquired. The second image is acquired either by fluoroscopy, echo cardiography, magnetic resonance imaging (MRI), or computer tomography (CT). Contour information is derived from the first image, either manually, by tracing around the ventricle contour, automatically, using a contour extraction algorithm, or semi-automatically.

The second image is superimposed on the contour of the first image showing the tip of catheter on the contour of the left ventricle. The superimposed image can be of either of the following types: a static contour image superimposed on a static catheter tip image, a static contour image superimposed on a dynamic catheter tip image, or a dynamic contour image superimposed on a dynamic catheter tip image. The locations within the heart chamber at which the condition information of the heart chamber is to be acquired, can be marked on a display, in order to provide the cardiologist with a visual indication of all the points at which the condition information is to be acquired.

U.S. Pat. No. 6,317,621 B1 issued to Graumann et al., and entitled "Method and Device for Catheter Navigation in Three-Dimensional Vascular Tree Exposures", is directed to a method for navigating a catheter within the brain of a patient, according to an image of the brain, without intraoperative radioscopic exposure and without administering an intraoperative contrast agent. A plurality of markers are attached to the outer periphery of the head of the patient. Transmitter coils of a position detection system are arranged in the vicinity of the patient and a receiver is built into the tip of the catheter. At least two two-dimensional projection images of the head of the patient are produced, by irradiating the head of the patient from different directions, by employing a C-arm X-ray device.

Each two-dimensional projection image includes an image of each of the markers. The respective marker position images are projected back, with the aid of projection image-specific projection matrices. The position of each of the markers in a three-dimensional image is determined according to the intersecting volume of the projection cones of the markers. The marker positions in the three-dimensional image is registered with the tip of the catheter, by approaching each of the markers in the three-dimensional image with a mouse, and touching the same markers with the tip of the catheter. A display displays the tip of the catheter mixed into the three-dimensional image of the vascular tree generated by segmentation, and subsequent volume rendering.

BRIEF DESCRIPTION OF THE DRAWINGS

The disclosed technique will be understood and appreciated more fully from the following detailed description taken in conjunction with the drawings in which:

FIG. 4A is a schematic illustration of a two-dimensional image of the lumen of FIG. 1A, at activity-state $T_1$ of an inspected organ;

FIG. 4B is a schematic illustration of another two-dimensional image of the lumen of FIG. 1A at activity-state $T_2$;

FIG. 4C is a schematic illustration of a further two-dimensional image of the lumen of FIG. 1A at activity-state $T_3$;

FIG. 4D is a schematic illustration of a GUI which includes a real-time substantially stabilized representation of an MPS sensor of a catheter located within the lumen of FIG. 1A, superimposed on the lumen of FIG. 4B, the GUI being constructed and operative according to a further embodiment of the disclosed technique;

FIG. 10A is a schematic illustration of a cardiac trajectory, in an electrical signal representation and in a mechanical signal representation;

FIG. 13 is a schematic illustration of a system constructed and operative in accordance with a further embodiment of the disclosed technique;

DETAILED DESCRIPTION OF THE EMBODIMENTS

Figure 1B:
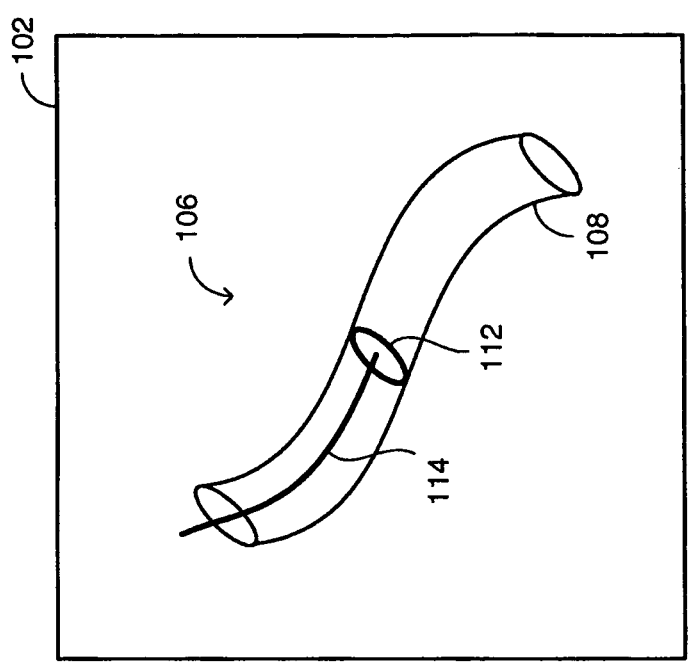
FIG. 1B is a schematic illustration of a GUI displaying another representation of the medical device on a three-dimensional image of a lumen of the lumen system of FIG. 1A, constructed and operative according to another embodiment of the disclosed technique.

The disclosed technique overcomes the disadvantages of the prior art by graphically designating on an image of the lumen, the position where a medical device (e.g., a PCI device, a dilation balloon, a stent delivery system) has to be delivered, and indicating when the medical device has reached the selected position. The medical device is attached to the tip of a catheter. A medical positioning system (MPS) sensor constantly detects the position of the medical device relative to the selected position. This position is represented on a real-time image (e.g., live fluoroscopy), a pseudo-real-time image (e.g., previously recorded cine-loop) or a previously recorded still image frame of the lumen, thereby obviating the need to radiate the inspected organ of the patient repeatedly, neither or to repeatedly inject contrast agent to the body of the patient. The medical staff can either guide the catheter manually according to feedback from an appropriate user interface, such as display, audio output, and the like, or activate a catheter guiding system which automatically guides the catheter toward the selected position.

The term "position" herein below, refers to the location of a point in space, the orientation of the point in space, or a combination thereof. The term "lumen" herein below, refers to an organic tubular structure of the human patient or the operated animal, such as an artery, vein, cardiac vessel, brain vessel, part of the urogenital system, nephrotic system, hepatic system, bronchus tree, and the like. The term "medical device" herein below refers to one which is employed to perform a minimally invasive operation within a lumen of the body of a patient. The medical device can be a vessel expansion unit such as a dilation balloon, stent delivery system, balloon expanding stent, self expending stent, percutaneous valve system, percutaneous coronary intervention (PCI) device, an ablation unit such as laser, cryogenic fluid unit, electric impulse unit, cutting balloon, rotational atherectomy unit (i.e., rotablator), directional atherectomy unit, transluminal extraction unit, a substance delivery unit such as coated or drug eluting metal stent, bio-absorbable stent, drug delivery balloon, brachytherapy unit, guidewire, and the like. It is noted that the terms, "stent", and "PCI device" herein below, are provided as two different examples of a "medical device".

The term "organ timing signal" herein below, refers to a signal representing cardiac cycle of the heart or the respiratory cycle of the lungs. An organ timing signal can be extracted using traditional methods such as ECG monitor, respiration rate monitor, and the like, herein below referred to as "organ timing signal monitor". Alternatively, the organ timing signal can be acquired by measuring the movements of the lumen due to cardiac or respiratory cycles. The movements of the lumen due to the cardiac or the respiratory cycle, can be measured by the MPS sensor attached to the catheter. In this case, the MPS determines the respective organ timing signal, according to the method described herein below in connection with FIG. 9.

The term "cine-loop" herein below, refers to a prerecorded sequence of two-dimensional images of the lumen, which are played back over and over again (i.e., in a loop), in synchrony with the real-time organ timing signal of the inspected organ of the patient. The two-dimensional images are acquired by a two-dimensional image acquisition device, such as X-ray fluoroscopy, C-arm, and the like, and individually stored while being associated with the respective activity-state of the inspected organ, at the time of image acquisition. In each case, an angiogram is produced by acquiring the two-dimensional images, while a contrast agent, injected into the body of the patient, is in an active state. The term "perspective" herein below, refers to an image of the lumen, which is acquired from different viewing angles, acquired by a plurality of image acquisition devices of different types, acquired by a plurality of image acquisition devices of substantially identical types, or a combination thereof.

The term "image sequence" herein below, refers to a sequence of images of the lumen of the patient, acquired by an image acquisition device coupled with a processor. In case the system includes a plurality of image acquisition devices, each image acquisition device acquires a different set of image sequences. The processor can produce a still image of the lumen, by selecting an image among one of the image sequences. The image sequence can be two-dimensional (i.e., acquired by a two-dimensional image acquisition device). The term "navigation image" herein below, refers to an image which the operator views in order to maneuver the catheter within the lumen system. The navigation image can be either two-dimensional or three-dimensional. The navigation image can be either a still image, a real-time image, or a cine-loop of the lumen system.

Alternatively, the image sequence can be three-dimensional. In this case, the processor produces a three-dimensional image sequence by reconstructing a plurality of two-dimensional images, according to the organ timing signal of the inspected organ, and according to position data respective of the coordinates of each two-dimensional image, which the MPS determines according to an output of an MPS sensor. The processor can produce a still image (i.e., either two-dimensional or three-dimensional) of the lumen, by selecting an image among one of the image sequences.

The term "real-time image" herein below, refers to an image which the operator views in real-time in order to maneuver the catheter within the lumen system. The real-time image shows the lumen system with the catheter therein, in real-time. The real-time image can be either two-dimensional or three-dimensional. The term "medical positioning system" (MPS) herein below, refers to an electromagnetic position detection system which detects the position of an object, according to an output of a three-axis coil which responds to electromagnetic radiation of an electromagnetic transmitter.

Figure 1A:
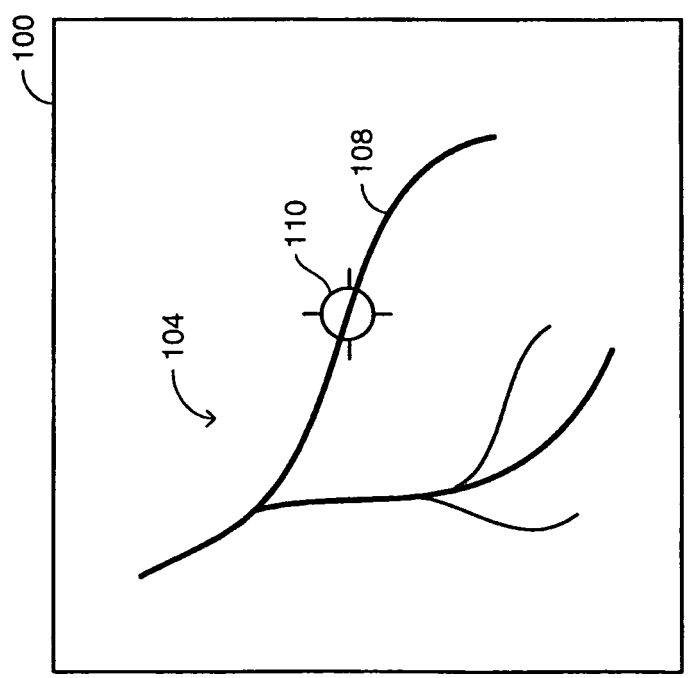
FIG. 1A is a schematic illustration of a graphical user interface (GUI) displaying a representation of a medical device on a two-dimensional image of a lumen system of the body of a patient, constructed and operative according to an embodiment of the disclosed technique.
Figure 2B:
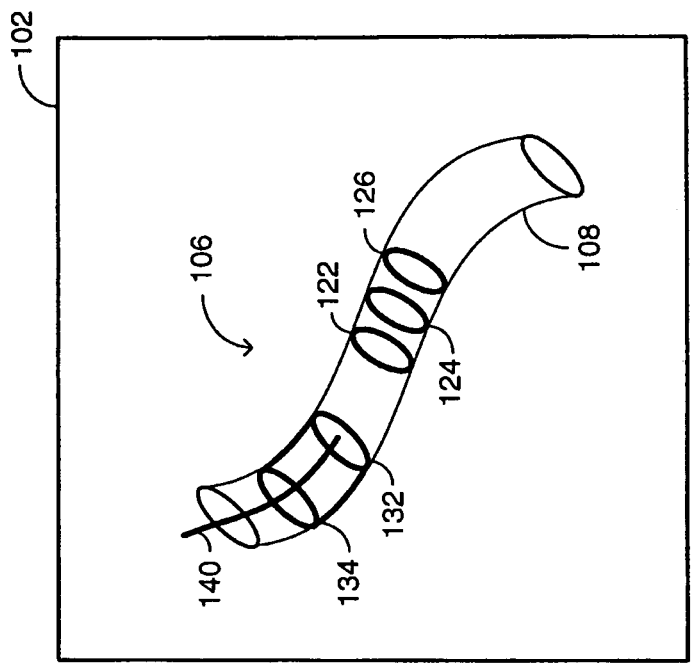
FIG. 2B is a schematic illustration of the GUI of FIG. 1B, displaying another set of marks equivalent to the set of marks of FIG. 2A, and another representation of the current position of the medical device, on the three-dimensional image of FIG. 1B.
Figure 2A:
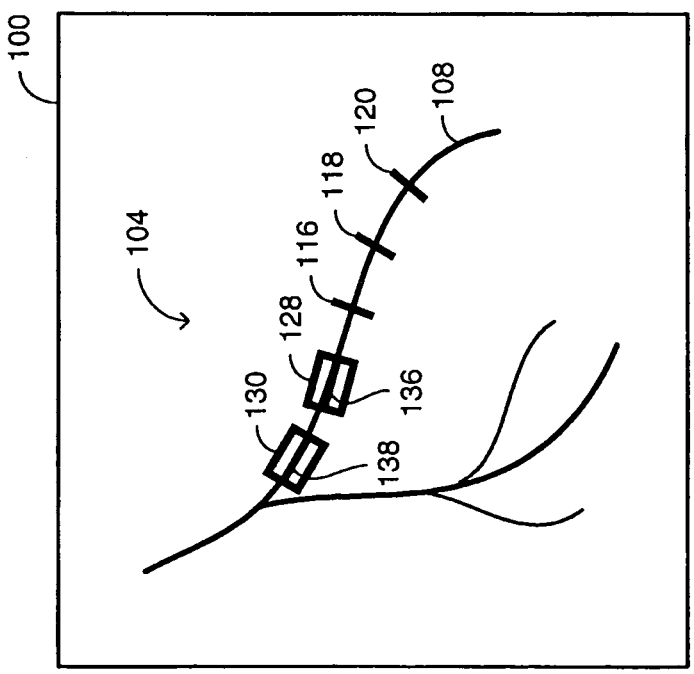
FIG. 2A is a schematic illustration of the GUI of FIG. 1A, displaying a set of marks respective of a selected position within the lumen system and a representation of the current position of the medical device advancing toward the selected location, on the two-dimensional image of FIG. 1A.
Figure 3B:
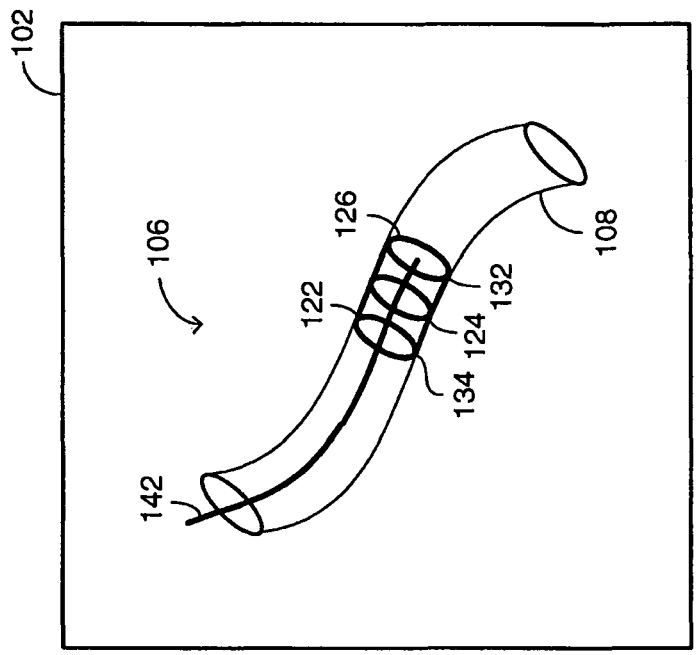
FIG. 3B is a schematic illustration of the GUI of FIG. 1B when the medical device reaches the selected position.
Figure 3A:
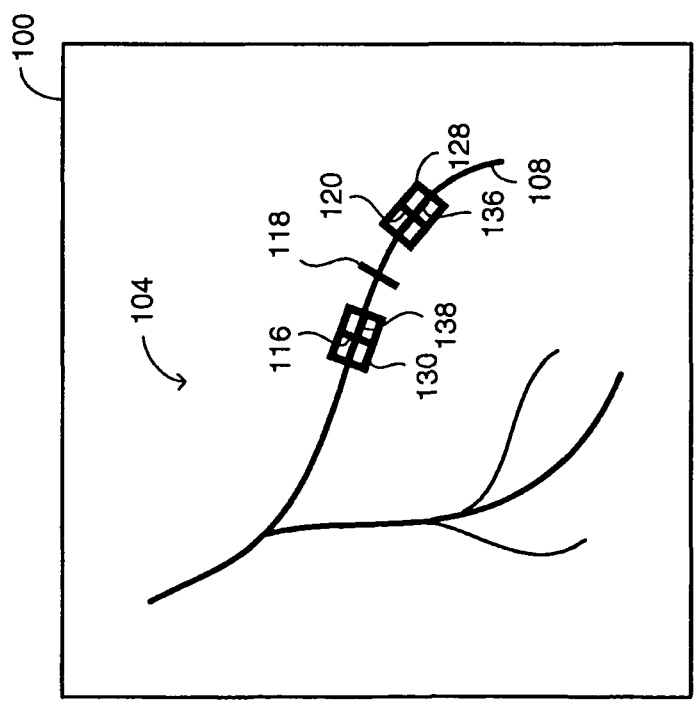
FIG. 3A is a schematic illustration of the GUI of FIG. 1A when the medical device reaches the selected position.

Reference is now made to FIGS. 1A, 1B, 2A, 2B, 3A, and 3B. FIG. 1A is a schematic illustration of a graphical user interface (GUI) generally referenced 100, displaying a representation of a medical device on a two-dimensional image of a lumen system of the body of a patient, constructed and operative according to an embodiment of the disclosed technique. FIG. 1B is a schematic illustration of a GUI generally referenced 102, displaying another representation of the medical device on a three-dimensional image of a lumen of the lumen system of FIG. 1A, constructed and operative according to another embodiment of the disclosed technique. FIG. 2A is a schematic illustration of the GUI of FIG. 1A, displaying a set of marks respective of a selected position within the lumen system and a representation of the current position of the medical device advancing toward the selected location, on the two-dimensional image of FIG. 1A. FIG. 2B is a schematic illustration of the GUI of FIG. 1B, displaying another set of marks equivalent to the set of marks of FIG. 2A, and another representation of the current position of the medical device, on the three-dimensional image of FIG. 1B. FIG. 3A is a schematic illustration of the GUI of FIG. 1A when the medical device reaches the selected position. FIG. 3B is a schematic illustration of the GUI of FIG. 1B when the medical device reaches the selected position.

With reference to FIG. 1A, while a lumen system (e.g., the coronary arteries—not shown) of the body of a patient (not shown) is imaged by a plurality of two-dimensional image acquisition devices (not shown), the operator (i.e., physical staff) inserts a catheter (not shown) into the lumen system.

GUI 100 includes a two-dimensional image 104 of the lumen system, as detected by the respective two-dimensional image acquisition device.

Two-dimensional image 104 can be an X-ray fluoroscopy, (i.e., angiogram), ultrasound image, an image detected by an optical coherent tomography detector—OCT, and the like. In case of X-ray fluoroscopy or angiogram, two-dimensional image 104 is a real-time image which is acquired from the lumen system, while a contrast agent is present in the lumen system. The ultrasound image is acquired during pull-back of the catheter within the same lumen system, which is known in the art as a virtual intravascular ultrasound (i.e., virtual IVUS) image. The virtual IVUS image can be displayed together with a real-time image of the lumen system. The virtual IVUS image can be either a still image of the lumen system, or a cine-loop thereof (i.e., an image sequence). The virtual IVUS image of the lumen system corresponds to the current position of the catheter within the lumen system, as detected by an MPS sensor (not shown), located at the tip of the catheter. This virtual IVUS image can be displayed at a selected phase of the organ timing signal of an organ (not shown) of the patient. Hence, two-dimensional image 104 can be either a real-time image, a still image, or a cine-loop.

The cine-loop can be acquired from a viewing angle different than the real-time image, thereby providing the operator with a real-time view of the lumen system from one viewing angle and a cine-loop view (i.e., a navigation image) from a different viewing angle of the same portion of the lumen system (i.e., bi-plane mode operation). Alternatively, the bi-plane mode can include two cine-loops each acquired from two different viewing angles, thereby providing the operator with two cine-loops acquired from two different viewing angles. It is noted that more than two different sets of images from more than two different viewing angles can be employed, thereby enabling a multi-plane operation mode.

Two-dimensional image 104 can be a still image of the lumen system (i.e., one of the images among a plurality of images in a cine-loop, which the operator selects). In this case, the selected two-dimensional image can be an image whose contrast for example, is better (e.g., the difference in the brightness of the dark pixels and the bright pixels in the image, is large) than all the rest, and which portrays the lumen system in a manner which is satisfactory for the operator either to designate the selected location of the medical device, or to view a real-time representation of the stent, as the medical device is being navigated within the lumen system.

With reference to FIG. 1B, GUI 102 includes a three-dimensional image 106 of a lumen (referenced 108) of the lumen system displayed in GUI 100, through which the catheter is being maneuvered. Three-dimensional image 106 is reconstructed from a plurality of two-dimensional images which are detected by a two-dimensional image acquisition device, during an image acquisition stage, by a technique known in the art.

Three-dimensional image 106 is a three-dimensional cine-loop (i.e., a navigation image) of lumen 108, which is played back in a loop, in synchrony with the real-time organ timing signal of the inspected organ. Alternatively, three-dimensional image 106 is a still image of lumen 108, which is selected among a plurality of three-dimensional images in the cine-loop. The operator can select the still image by playing the cine-loop forward and backward. Further alternatively, three-dimensional image 106 is a still image of lumen 108, frozen at a selected activity-state of the inspected organ.

Three-dimensional image 106 is synchronized with a real-time organ timing signal (e.g., cardiac cycle) respective of the movement of the inspected organ (e.g., the inspected lumen—not shown). The organ timing signal can be acquired for example, by an ECG monitor (not shown) coupled with the patient. Alternatively, the organ timing signal (e.g., the heart beat or the respiration of the patient) can be determined by the MPS (not shown), as described herein below in connection with FIGS. 9, 10A, and 10B.

A system according to the disclosed technique can display a selected image sequence (either a sequence of two-dimensional images detected by the respective two-dimensional image acquisition device, or a sequence of three-dimensional images reconstructed from a plurality of two-dimensional images—i.e., a cine-loop or video clip), in synchrony with the real-time organ timing signal of the patient, among a list of prerecorded image sequences. The system can display a still image among a selected image sequence. Alternatively, the system can display a real-time two-dimensional image of the inspected organ, acquired from a first viewing angle by one of the two-dimensional image acquisition devices, alongside a navigation two-dimensional image sequence (i.e., two-dimensional cine-loop) of the inspected organ, acquired previously by either the same two-dimensional image acquisition device or another two-dimensional image acquisition device, from a second viewing angle, and played back in synchrony with the real-time organ timing signal of the inspected organ.

The operator can view a prerecorded two-dimensional image sequence (e.g., an X-ray fluoroscopy) synchronized with the real-time organ timing signal of the organ, thereby obviating the need to inject a contrast agent repeatedly and subjecting the patient and the operator to unnecessary radiation. Alternatively, the system can display the image relative to a selected activity-state of the organ (i.e., a still image), as described herein below in connection with FIG. 7.

An MPS sensor (not shown) is firmly attached to the tip of the catheter. Three-dimensional image 106 is registered with two-dimensional image 104, such that each point in two-dimensional image 104 corresponds to a respective point in three-dimensional image 106. In this manner, the coordinates of each point in three-dimensional image 106 can be projected onto two-dimensional image 104. Alternatively, each point in two-dimensional image 104 can be transferred to three-dimensional image 106 (e.g., by acquiring a series of two-dimensional images from different viewing angles). A real-time representation 110 (FIG. 1A) of the MPS sensor is superimposed on lumen 108, as described herein below in connection with FIG. 6C. A real-time representation 112 (FIG. 1B) of the MPS sensor is superimposed on three-dimensional image 106.

In addition to real-time representation 110, the operator can view one or more radio-opaque markers (e.g., metallic band) attached to the catheter, on a real-time two-dimensional image of lumen 108. This feature enables the operator to continue using the real-time two-dimensional image, even when little or no contrast agent exists within lumen 108, or when the contrast agent within lumen 108 is unnoticeable.

A trajectory 114 (FIG. 1B) of the catheter as advanced through lumen 108 is constructed and represented in GUI 102, as described herein below in connection with FIGS. 6B, and 6C. Trajectory 114 is constantly updated in synchrony with the movement of lumen 108, according to the position data acquired by the MPS sensor. Moreover, in this manner, three-dimensional image 106 is displayed relative to the coordinate system of lumen 108. The movement of lumen 108 can be caused for example, by the heart beat, the respiration, contraction of nearby muscles of the patient, and the like.

The operator can direct the system via a user interface (not shown), to alternately display GUI 100 and GUI 102, on the display. The user interface can be a switch, foot pedal, and the like, as described herein below in connection with FIG. 4D. Alternatively, the display can display GUI 100 and GUI 102 at the same time, side by side. Further alternatively, the system can include a plurality of displays coupled with the processor, each display displaying different image sequences. The operator can direct the system to display a real-time two-dimensional image of the lumen system, for example, by pressing the foot pedal, thereby activating the respective two-dimensional image acquisition device. Alternatively, the operator can direct the system via the user interface, to display a previous two-dimensional cine-loop of the lumen system, instead of the real-time two-dimensional image of the lumen system. In this case, the system displays the two-dimensional cine-loop which was last played back. If the system includes no cine-loops (i.e., prerecorded time-tagged image sequences), then the system displays a cine-loop of the most recent real-time two-dimensional image. Further alternatively, the operator can direct the system to display the real-time two-dimensional image and a selected cine-loop, on the same display, side by side.

With the aid of GUI 100 and GUI 102, the operator maneuvers the catheter manually, in order to reach a predetermined region within the lumen system. Alternatively, the operator can employ an automatic system (not shown) for automatically maneuvering the catheter to the predetermined region, as described herein below in connection with FIGS. 11, and 12.

With reference to FIG. 2A, during a planning session, the operator graphically designates a plurality of marks 116, 118, and 120 on two-dimensional image 104, as a selected position within lumen 108, which a medical device (not shown) is to be delivered to. The operator performs the marking either on a frozen two-dimensional image of lumen 108, or on a frozen reconstructed three-dimensional model of lumen 108. The operator performs the marking in different manners, such as manually, according to an automated two-dimensional or three-dimensional quantitative cardiac assessment (QCA), and the like.

During the planning session, a respective one of a plurality of displays (not shown) displays a superposition of a trajectory of a catheter previously maneuvered through lumen 108, on an image of lumen 108. The trajectory can be displayed either on two-dimensional image 104 or three-dimensional image 106 (e.g., trajectory 114).

This trajectory can be obtained for example, by employing a guided intravascular ultrasound catheter (GIVUS—not shown), in an imaging session prior to the planning session. The GIVUS is a catheter which includes an image detector (e.g., ultrasound transducer) at the tip thereof, and an MPS sensor in the vicinity of the image detector. The operator maneuvers the GIVUS within the lumen, as far as physically possible, and then pulls the GIVUS back through the lumen. During the pull-back, the image detector detects a plurality of two-dimensional images of the inside of the lumen.

The system associates each of the two-dimensional images with the respective position of the image detector determined by the MPS, and with the respective activity-state of the inspected organ. The system can determine a cine-loop of the trajectory during the pull-back, and the operator can select a frozen trajectory to be employed during the planning session. The system can further reconstruct three-dimensional image 106 according to the time-tagged two-dimensional images acquired by the GIVUS.

During the planning session, a respective one of the displays displays marks 116, 118 and 120 articulated by the user interface on an image of lumen 108. The operator can move marks 116, 118 and 120 together along the full length of the trajectory (e.g., trajectory 114 of FIG. 1B). Mark 118 designates the middle of the medical device, while marks 116 and 120 designate the rear end and the front end of the medical device, respectively. The system determines the distance between marks 116 and 120, according to the type (e.g., the size of stent) which the operator has selected. Marks 116, 118 and 120 together, are locked-on to the trajectory, while being operative to travel along the trajectory. The operator designates the position of mark 118 along the trajectory where the medical device is to be delivered to.

For simplicity, the medical device in the example set forth in FIGS. 2A, 2B, 3A, and 3B, is a stent. In this case, each of marks 116, 118, and 120 is a substantially straight line, which is substantially perpendicular to lumen 108. For example, marks 116 and 120 designate the two ends of the stent, while mark 118 designates the middle of the stent. Marks 116, 118, and 120 define the location of the stent in lumen 108, as well as the orientation thereof. The marking is performed via a user interface (not shown), such as a joystick, push button, pointing device (e.g., a mouse, stylus and digital tablet, track-ball, touch pad), and the like.

A plurality of marks 122, 124 and 126, which are the counterpart of marks 116, 118, and 120, respectively, are simultaneously displayed on three-dimensional image 106 in GUI 102. For the purpose of performing the marking, each of two-dimensional image 104 and three-dimensional image 106 is frozen at the same activity-state of the inspected organ (e.g., the heart). This freezing feature provides a still image of lumen 108, thereby preventing vibrations of the image and enabling a successful marking by the operator.

Instead of manually designating the marks, an algorithm can be employed to automatically identify the selected location (e.g., by entering into the algorithm, a selected percentage of occlusion by a plaque in a lumen), and designate marks 116, 118, 120, 122, 124, and 126, automatically. This aspect of the invention is described herein below in connection with FIGS. 8A, 8B, and 8C. The system associates the occlusion data with three-dimensional image 106, and projects this occlusion data on two-dimensional image 104, for the purpose of designating marks 116, 118 and 120.

During the medical operation, following the planning session, a catheter which includes a stent (not shown), is maneuvered within lumen 108 toward marks 116, 118 and 120. An MPS sensor (not shown) is attached to the catheter in the vicinity of the stent. With reference to FIGS. 2A and 2B, the position of the front end and of the rear end of the stent are represented in real-time, by features 128 and 130, respectively, on two-dimensional image 104, and by features 132 and 134, respectively, on three-dimensional image 106. In the example set forth in FIGS. 2A and 2B, each of features 128 and 130 is in form of a rectangle with longitudinal lines 136 and 138, respectively, dividing each rectangle in two. The actual trajectory of the catheter is represented by a feature 140 (FIG. 2B) superimposed on three-dimensional image 106. The actual trajectory of the catheter can be represented by another feature (not shown) superimposed on two-dimensional image 104.

During the medical operation, the system superimposes features 128 and 130 together with marks 116, 118 and 120, while the catheter is being maneuvered through lumen 108, either on a real-time two-dimensional image of lumen 108 (e.g., angiogram), on a two-dimensional cine-loop of lumen 108, or on a frozen two-dimensional image of lumen 108. Additionally, the system superimposes features 132 and 134 together with marks 122, 124 and 126, while the catheter is being maneuvered through lumen 108, either on a real-time three-dimensional image of lumen 108, on a still three-dimensional image of lumen 108, or on a cine-loop of lumen 108. Further additionally, the system superimposes features 132 and 134 together with marks 122, 124 and 126, on the real-time two-dimensional image of lumen 108, as well as one or more navigation images of lumen 108 (e.g., virtual IVUS image—either a still image or a cine-loop), acquired from viewing angles different than that of the real-time two-dimensional image.

The system determines the distance between the centers (not shown) of features 128 and 130, according to the type (i.e., size) of stent which the operator selects for mounting in lumen 108. This distance as displayed on the respective one of the displays, is substantially fixed, as the stent is maneuvered through lumen 108. Features 128 and 130 move together on image 104, while the stent is maneuvered through lumen 108. A respective one of the displays can display trajectories 140 and 142, either while a catheter (not shown) is being maneuvered through lumen 108, or during a play-back session, after performing the medical operation on the patient.

It is noted that the system superimposes features 128, 130, 132, and 134, and marks 116, 118, 120, 122, 124, and 126, on the respective image of lumen 108, according to the real-time organ timing signal of the inspected organ (i.e., the system takes into account the movements of lumen 108 due to the movements of the inspected organ, while the catheter is being maneuvered through lumen 108). This aspect of the disclosed technique enables the system to display marks 116, 118, 120, 122, 124, and 126, on a vibrating image of lumen 108, at substantially the same position which the operator had initially designated relative to lumen 108. If the system did not operate in this manner, then marks 116, 118, 120, 122, 124, and 126, would be non-stationary relative to a vibrating image of lumen 108. Likewise, features 128, 130, 132, and 134, are substantially stationary relative to the vibrating image of lumen 108.

It is further noted that the operator can direct the system to either turn on or turn off the display of superposition of any of the marks, the representation of the position of the stent, the trajectory, or a combination thereof, via the user interface. Any attribute can be selected to represent the marks and the representation of the stent, as long as they are different, such as color, shape, size, and the like. However, a mark or a stent representation is displayed by the same attribute both in two-dimensional image 104 and three-dimensional image 106. For example, marks 116, 118, 120, 122, 124, and 126 are represented in green, features 128, 130, 132, and 134 are represented in blue, and trajectory 140 is represented in red.

With reference to FIGS. 3A and 3B, while the catheter is being maneuvered through lumen 108, each of two-dimensional image 104 and three-dimensional image 106, is displayed relative to the coordinate system of lumen 108 (i.e., relative to the MPS sensor which is attached to the catheter, and which constantly moves together with lumen 108). When the stent reaches the selected position (i.e., front end of the stent is substantially aligned with mark 120 and the rear end thereof is substantially aligned with mark 116), a user interface (e.g., audio, visual, or tactile device—not shown) announces the event to the operator.

In the example set forth in FIG. 3A, when the stent is aligned with the selected position, each pair of longitudinal lines and marks turns into a cross (i.e., longitudinal line 136 together with mark 120 forms one cross, and longitudinal line 138 together with mark 116 forms another cross). Additionally, the user interface can produce a relatively weak output, or a relatively strong output, when the stent is receding from the selected location, or approaching the selected location, respectively. For example, as the distance between the stent and mark 118 decreases, the volume of the audio signal is increased, and otherwise, the volume is decreased. A trajectory of the catheter while being maneuvered toward the selected location, is represented by a feature referenced 142 (FIG. 3B) superimposed on three-dimensional image 106.

Reference is further made to FIGS. 4A, 4B, 4C, and 4D. FIG. 4A is a schematic illustration of an image, generally referenced 144, of the lumen of FIG. 1A, at activity-state $T_1$ of an inspected organ. FIG. 4B is a schematic illustration of another image, generally referenced 146, of the lumen of FIG. 1A at activity-state $T_2$. FIG. 4C is a schematic illustration of a further image, generally referenced 148, of the lumen of FIG. 1A at activity-state $T_3$. FIG. 4D is a schematic illustration of a GUI generally referenced 150, which includes a real-time substantially stabilized representation of an MPS sensor of a catheter located within the lumen of FIG. 1A, superimposed on the lumen of FIG. 4B, the GUI being constructed and operative according to a further embodiment of the disclosed technique.

Each of images 144, 146, and 148 in the description herein below can be either a two-dimensional image or a three-dimensional image. Images 144, 146 and 148 belong to a set of images of lumen 108 (FIG. 1A), acquired prior to the planning session. With reference to FIG. 4B, lumen 108 at activity-state $T_2$, represented by a point 152 has moved by a distance $S_1$ along the negative Y axis, relative to the position thereof at activity-state $T_1$. With reference to FIG. 4C, lumen 108 at activity-state $T_3$ has moved by a distance $S_2$ along the negative Y axis, relative to the position thereof at activity-state $T_2$.

The contrast agent which is injected into the lumen system of the patient remains within lumen 108 for a substantially short period of time. During this period of time, the contrast of the set of the images gradually increases to a peak and then gradually decreases, until the image disappears altogether. The operator selects one of the images 144, 146 and 148 (e.g., image 146), in order to designate marks 116, 118 and 120 (FIG. 2A), and later observes the real-time advancement of the catheter represented by features 128 and 130, superimposed on image 146. The operator selects image 146, for example, because the contrast ratio thereof is greater than that of images 144 and 148, features 128 and 130 are most clearly visible in image 146, than in images 144 and 148, and the like. Image 146 (FIG. 4D) is an image of lumen 108 at activity-state $T_2$.

Alternatively, the system compensates for the movement of lumen 108 due to the cycle of the inspected organ (e.g., the cardiac cycle), in order to superimpose a substantially static real-time representation of the medical device on an image (not shown) of lumen 108, which is also substantially static. In this case, the system produces the image in the coordinate system of the MPS sensor which is attached to the catheter. Hence, the operator can view a substantially static image of lumen 108, along with the real-time substantially static representation of the medical device, despite the actual movements of lumen 108 due to the cycle of the inspected organ. It is noted that in the absence of this technique, the operator would view an unstable rapidly vibrating image of lumen 108, together with the real-time representation of the medical device, which is distracting to the eyes.

With reference to FIG. 4D, GUI 150 displays a real-time representation 154 of the medical device superimposed on an image of lumen 108 frozen at activity-state $T_2$, while representation 154 is substantially static at all activity-states, including activity-states $T_1$ and $T_2$. In this case, the system produces image 146 in a presentation coordinate system, in which the MPS sensor is substantially stationary (e.g., the stent is fixed in the center of the image, while the scenery around it changes, as the stent is moved within the lumen). It is noted that according to this aspect of the disclosed technique, the system is capable to display a substantially static representation of the medical device, substantially free of vibrations due to the cardiac cycle. In this manner, the system maintains a superposition of representation 154 on the image of lumen 108, within the boundaries of that image, while the catheter is maneuvered through lumen 108. In case the movements due to the cardiac cycle were not compensated for, representation 154 would erratically move back and forth between points 156 and 158 (corresponding to distances $S_1$ and $S_2$, respectively), which are distracting to the operator.

Alternatively, the system can superimpose only that representation of the medical device, which corresponds to the activity-state respective of the frozen image of lumen 108, and neglect all other activity-states of lumen 108. With reference to FIG. 4D, the system can superimpose representation 154 on the image of lumen 108, only when representation 154 corresponds to activity-state $T_2$. This type of display still provides a substantially satisfactory view for the operator, since for example, at substantially rapid rates of the cardiac cycle, this loss of data is substantially imperceptible to the human eye.

The system can determine the distances $S_1$ and $S_2$, according to a set of three-dimensional images reconstructed from a series of time-tagged two-dimensional images of lumen 108, acquired from inside of lumen 108 (e.g., by employing a GIVUS). Alternatively, the system can determine the distances $S_1$ and $S_2$ by processing and comparing among a set of two-dimensional images acquired from outside of lumen 108 (e.g., images 144, 146 and 148).

The operator can direct the system to switch between GUI 150 and a real-time two-dimensional image of lumen 108 (e.g., an angiogram), by employing a user interface (not shown—for example a foot pedal). When the operator presses the foot pedal, the two-dimensional image acquisition device radiates a portion of the body of the patient, and the system displays the real-time two-dimensional image instead of GUI 150. Alternatively, the system can superimpose the real-time two-dimensional image on GUI 150. Further alternatively, the system can display the real-time two-dimensional image along side GUI 150.

Figure 5:
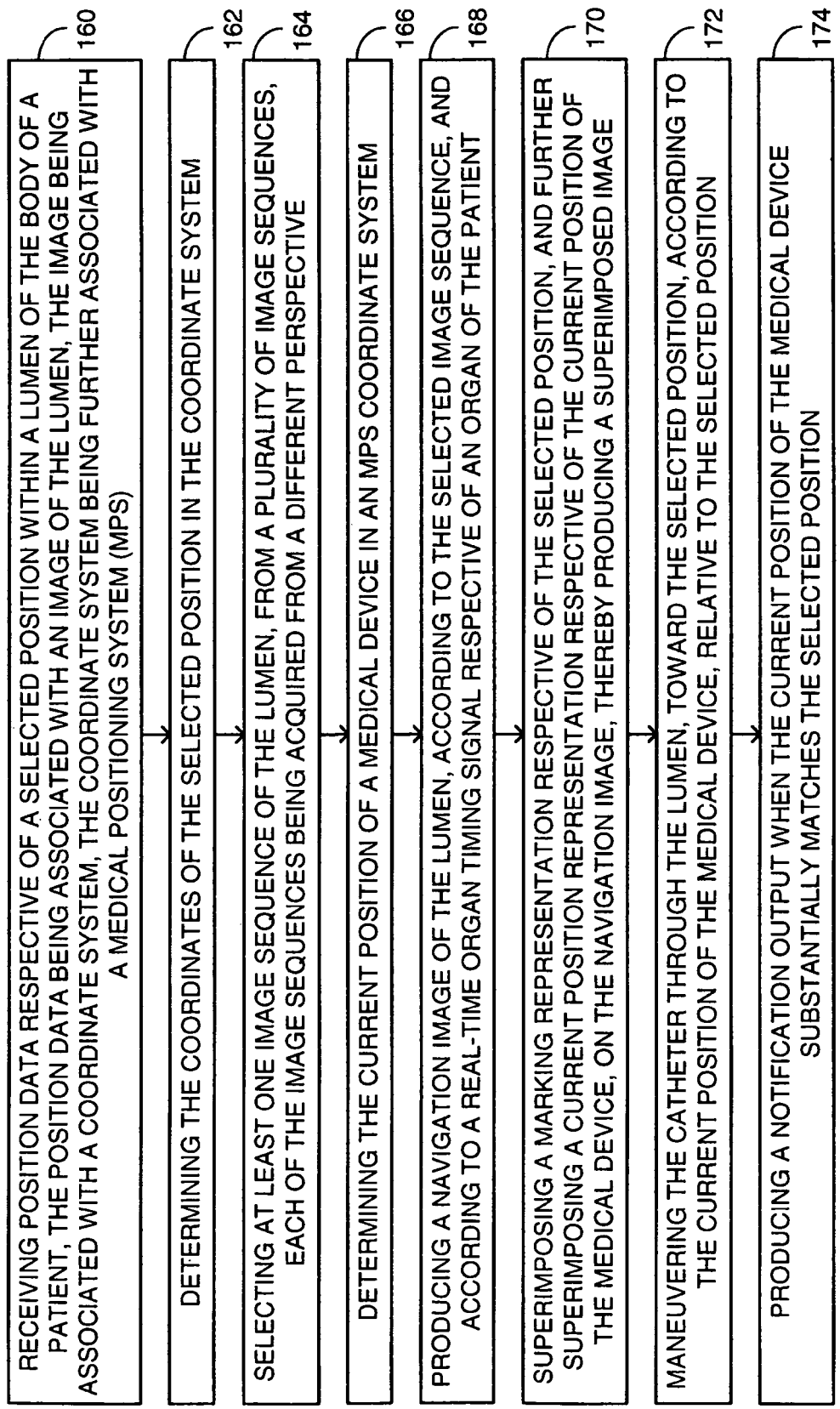
FIG. 5 is a schematic illustration of a method for delivering a medical device to a selected position within a lumen of the body of a patient, operative according to another embodiment of the disclosed technique.

Reference is now made to FIG. 5, which is a schematic illustration of a method for delivering a medical device to a selected position within a lumen of the body of a patient, operative according to another embodiment of the disclosed technique. In procedure 160, position data respective of a selected position within a lumen of the body of a patient is received, the position data being associated with an image of the lumen, the image being associated with a coordinate system, the coordinate system being further associated with a medical positioning system (MPS).

With reference to FIG. 2A, a processor of a system receives via a user interface, position data respective of marks 116, 118 and 120, which the operator designates on two-dimensional image 104. Marks 116, 118 and 120 designate the selected position within lumen 108, where the medical device is to be delivered to. Marks 116, 118, and 120 are associated with two-dimensional image 104, two-dimensional image 104 is associated with a coordinate system, and the coordinate system is further associated with the MPS. The processor determines the coordinates of marks 116, 118 and 120, in the MPS coordinate system (procedure 162). The processor further determines the coordinates of marks 122, 124, and 126 on three-dimensional image 106, in the MPS coordinate system, which are equivalent to marks 116, 118, and 120, respectively (procedure 162).

In procedure 164, at least one image sequence in selected from a plurality of image sequences, each of the image sequences being acquired from a different perspective. The processor selects an image sequence among a plurality of image sequences, each acquired by a different image acquisition device, from a different viewing angle, or a combination thereof.

In procedure 166, the current position of a medical device in an MPS coordinate system is determined. With reference to FIG. 1A, the MPS determines the current position of the medical device, in the MPS coordinate system, according to the output of the MPS sensor. This current position is represented by real-time representation 110.

In procedure 168, a navigation image of the lumen is produced, according to the selected image sequence, and according to a real-time organ timing signal respective of an organ of the patient. With reference to FIG. 2A, the processor produces two-dimensional image 104 according to the image sequence which the processor selects in procedure 164, and according to the real-time organ timing signal of an organ of the patient (e.g., the heart). Alternatively, with reference to FIG. 2B, the processor produces three-dimensional image 106 in a similar manner.

In procedure 170, a marking representation respective of the selected position, and a current position representation respective of the current position of the medical device, is superimposed on the navigation image, thereby producing a superimposed image. With reference to FIG. 2A, the processor produces two-dimensional image 104, by superimposing marks 116, 118, and 120, and further superimposing features 128 and 130 representative of the current position of the medical device, on the navigation image which the processor produces in procedure 168. The processor produces three-dimensional image 106 in a similar manner.

In procedure 172, the catheter is maneuvered through the lumen, toward the selected position, according to the current position of the medical device, relative to the selected position. With reference to FIG. 2A, the operator maneuvers the catheter toward the selected position, manually, by viewing features 128 and 130 on the display, as well as marks 116, 118, and 120. Alternatively, the operator maneuvers the catheter automatically or semi-automatically toward the selected position, as described herein below, in connection with FIG. 11. The processor produces a notification output, when the processor determines that the current position of the medical device substantially matches the selected position (procedure 174).

According to another embodiment of the disclosed technique, procedure 164 can be eliminated from the above mentioned method. In this case, in procedure 168, the processor produces the navigation image according to a single image sequence, where there is no provision for the operator to view different images of lumen 108 acquired from different viewing angles or by different image acquisition devices. According to a further embodiment of the disclosed technique, procedures 164, 168 and 170 are optional, wherein procedure 172 is performed without any visual aid to represent the lumen in which the catheter is maneuvered (i.e., analogous to instrument flying with zero visibility).

A system (not shown) can produce three-dimensional image 106 according to a plurality of two-dimensional images acquired by a two-dimensional image acquisition device, and according to the organ timing signal of lumen 108, and play back an image sequence of the three-dimensional image 106 in synchrony with the real-time organ timing signal. The system can play back also a cine-loop of lumen 108 in synchrony with the real-time organ timing signal, selected from a list of cine-loops. The system can display either of two-dimensional image 104 or three-dimensional image 106, relative to a selected activity-state of the organ timing signal (i.e., freezing an image).

The system can display either of two-dimensional image 104 or three-dimensional image 106, relative to the coordinate system of a selected MPS sensor (e.g., an MPS sensor attached to the catheter, an MPS sensor attached to the body of the patient, or an MPS attached to the operating table). The system can display a still image selected from a cine-loop sequence. The system can acquire the organ timing signal by processing the MPS data, instead of the data acquired by the ECG monitor. The system can display a representation of the position of the catheter superimposed on either two-dimensional image 104, or three-dimensional image 106, as well as the actual trajectory of the catheter within the lumen. The system can identify a plaque within lumen 108, having a selected percentage of occlusion, and automatically designate the position of the plaque by marks 116, 118 and 120.

The two-dimensional image acquisition device can be of any type known in the art, such as computerized tomography (CT), nuclear magnetic resonance (MRI), positron-emission tomography (PET), single-photon-emission computer tomography (SPECT), fluoroscopy (i.e., X-ray machine), C-arm, guided intra-vascular ultrasound (GIVUS), external ultrasound, optical coherent tomography (OCT) detector, and the like. Each of two-dimensional image acquisition devices acquires either a two-dimensional image of lumen 108 (FIG. 1A) from outside of the body of the patient (e.g., by employing a C-arm, CT, MRI), or a two-dimensional image of lumen 108 from within lumen 108 (e.g., by employing a GIVUS).

Following is a description of reconstructing the trajectory of a catheter within a lumen, according to detected positions of the catheter at a selected activity-state of the organ timing signal of the lumen. In this manner, a trajectory corresponding to the selected activity-state, can be displayed together with the three-dimensional image of the lumen corresponding to the same activity-state. Alternatively, a real-time three-dimensional image sequence of the lumen can be displayed according to the organ timing signal of the lumen, together with the corresponding trajectories.

Figure 6A:
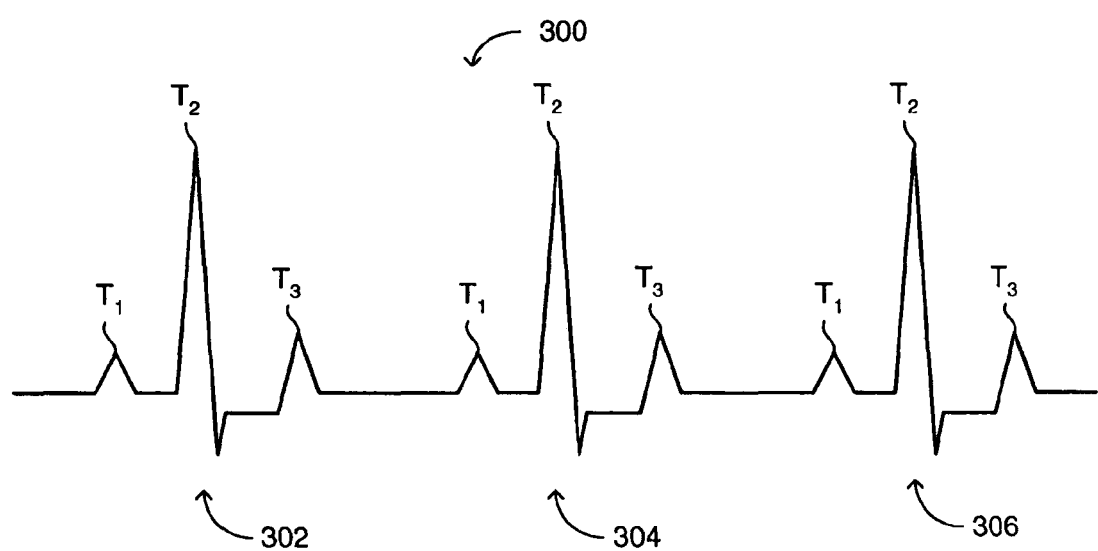
FIG. 6A is a schematic illustration of an ECG of a patient.
Figure 6B:
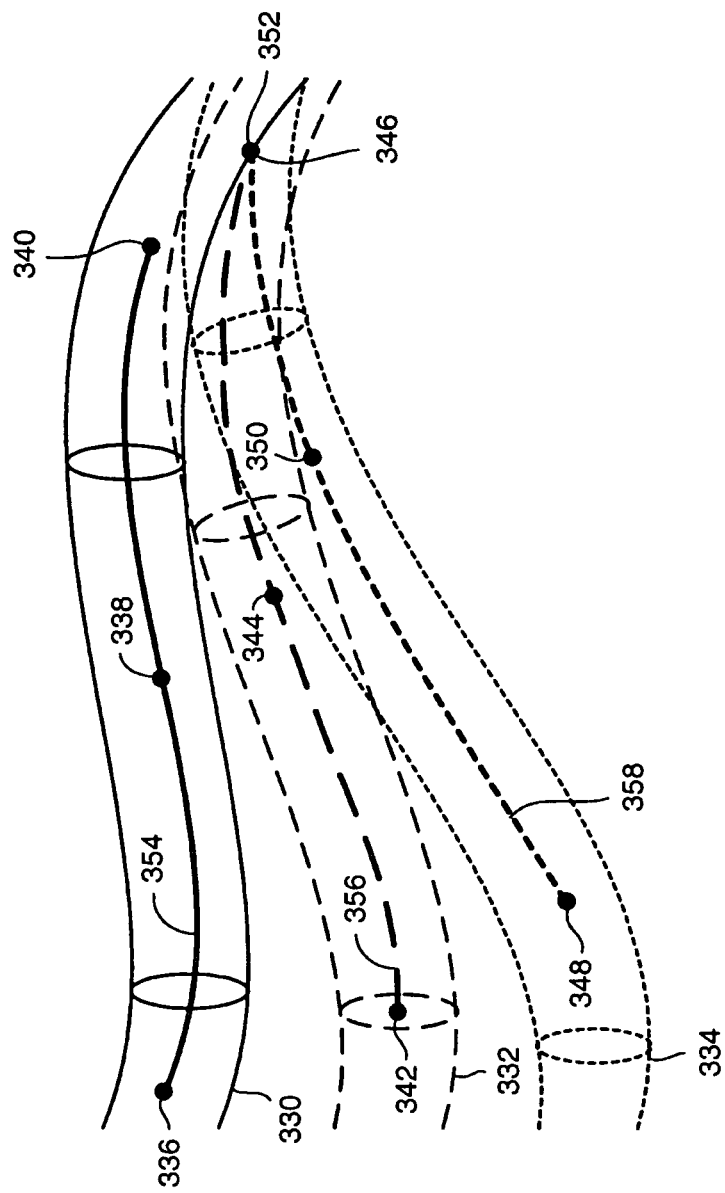
FIG. 6B is a schematic illustration of trajectories of the tip of a catheter located within the lumen of FIG. 1A, respective of different activity-states of the ECG of FIG. 6A, constructed according to another embodiment of the disclosed technique.
Figure 6C:
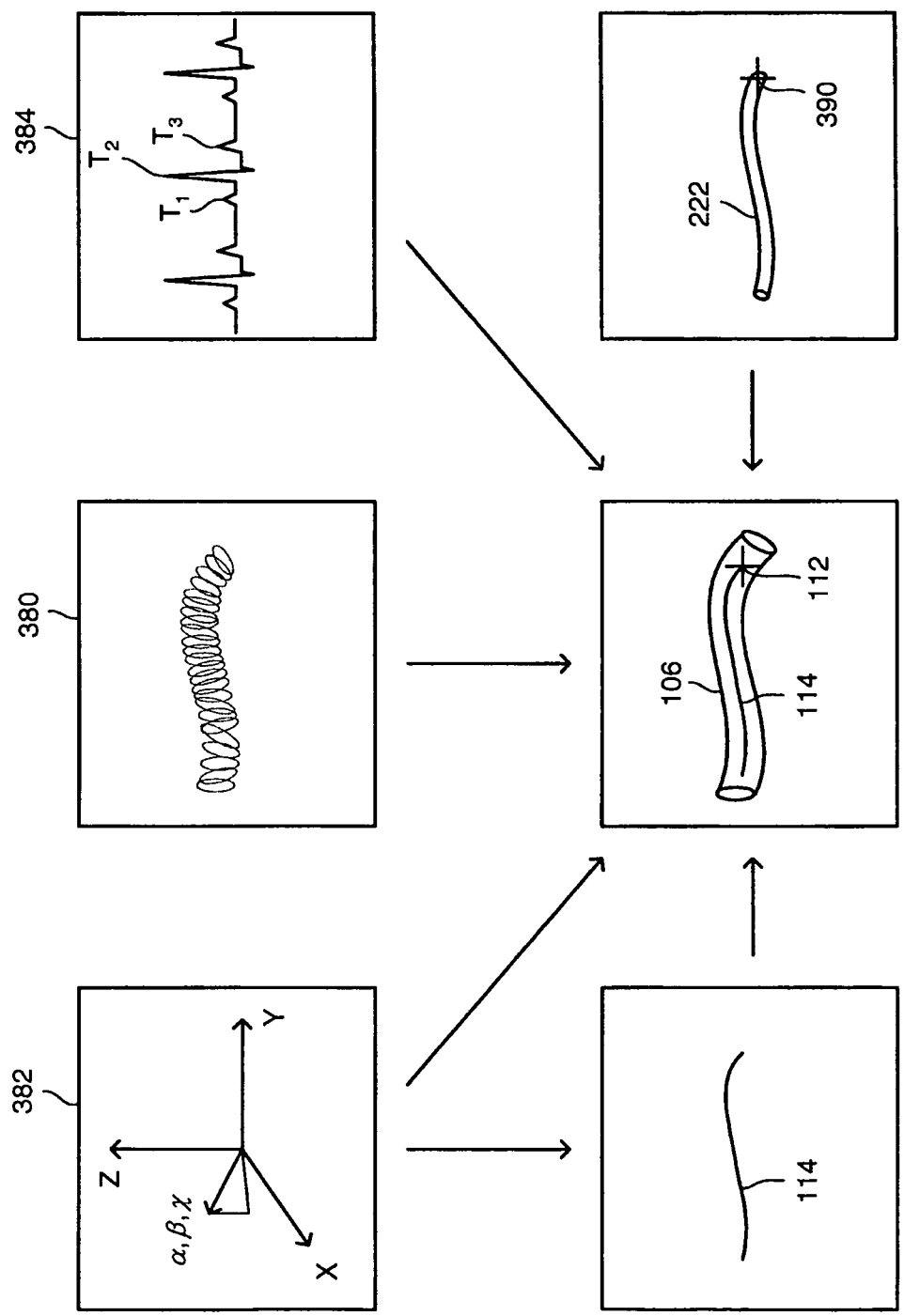
FIG. 6C is a schematic illustration of the process of reconstructing a three-dimensional organ motion dependent image sequence, and superimposing additional visual data thereon, by processing the signals received from the two-dimensional image acquisition device, the MPS and the ECG monitor.

Reference is further made to FIGS. 6A, 6B and 6C. FIG. 6A is a schematic illustration of an ECG of a patient, generally referenced 300. FIG. 6B is a schematic illustration of trajectories of the tip of a catheter located within the lumen of FIG. 1A, respective of different activity-states of an ECG 6A, constructed according to another embodiment of the disclosed technique. FIG. 6C is a schematic illustration of the process of reconstructing a three-dimensional organ motion dependent image sequence, and superimposing additional visual data thereon, by processing the signals received from the two-dimensional image acquisition device, the MPS and the ECG monitor. The additional visual data can include the position of the catheter within the lumen, the trajectory of a catheter within the lumen, and the like.

ECG 300 includes a plurality of activity-states (e.g. ECG cycle phases), such as activity-states $T_1$, $T_2$ and $T_3$ in each of a plurality of heart cycles 302, 304 and 306. Applicant has found that the position of lumen 108 (FIGS. 1A and 1B) is different at different activity-states, during each of the heart cycles 302, 304 and 306.

For example, at activity-state $T_1$ of each of the heart cycles 302, 304 and 306, the position of lumen 108 is represented by a lumen image at a position 330 (FIG. 6B). At activity-state $T_2$ of each of the heart cycles 302, 304 and 306, the position of lumen 108 is represented by a lumen image at a position 332. At activity-state $T_3$ of each of the heart cycles 302, 304 and 306, the position of lumen 108 is represented by a lumen image at a position 334. At position 330, points 336, 338 and 340 represent different positions of a catheter (not shown) at activity-state $T_1$. At position 332, points 342, 344 and 346 represent different positions of the catheter at activity-state $T_2$. At position 334, points 348, 350 and 352 represent different positions of the catheter at activity-state $T_3$.

A processor (not shown) associates between all of the two-dimensional images (i.e., images acquired at points 336, 338 and 340) which were detected during activity-state $T_1$ at any cycle of ECG signal 300. Similarly, processor 192 associates between all of the two-dimensional images (i.e., images acquired at points 342, 344 and 346) which were detected during activity-state $T_2$ at any cycle of ECG 300 and further associates between all of the two-dimensional images (i.e., images acquired at points 348, 350 and 352) which were detected during activity-state $T_3$ at any cycle of ECG 300.

The processor reconstructs a three-dimensional image from all of the two-dimensional images, which were associated with respect to a given activity-state $T_i$. With reference to FIG. 6B, the processor reconstructs three-dimensional image 330, which is the image of the inspected organ at activity-state $T_1$ (FIG. 6A), and three-dimensional image 332, which is the image of the inspected organ at activity-state $T_2$. Likewise, the processor reconstructs three-dimensional image 334, which is the image of the inspected organ at activity-state $T_3$.

The processor calculates a trajectory 354 from points 336, 338 and 340, associated with activity-state $T_1$. Similarly, the processor calculates a trajectory 356 from points 342, 344 and 346 associated with activity-state $T_2$ and further calculates a trajectory 358 from points 348, 350 and 352 associated with activity-state $T_3$.

The processor associates between each of the calculated trajectories and one of the reconstructed three-dimensional images, respective of a given organ activity-state. With reference to FIG. 6B, the processor associates between trajectory 354 and reconstructed three-dimensional image 330, respective of activity-state $T_1$. Similarly, the processor associates between trajectory 356 and reconstructed three-dimensional image 332, respective of activity state $T_2$ and further between trajectory 358 and reconstructed three-dimensional image 334, respective of activity-state $T_3$.

Since points 336, 338, 340, 342, 344, 346, 348, 350 and 352, used for calculating the trajectories are also the points at which their respective two-dimensional images were acquired, the processor can superimpose each of the calculated trajectories on its respective reconstructed three-dimensional image. For example, the processor superimposes trajectory 354 on three-dimensional image 330, trajectory 356 on three-dimensional image 332 and trajectory 358 on three-dimensional image 334.

With reference to FIG. 6C, the processor reconstructs three-dimensional image 106 (FIG. 1B) of lumen 108, from a plurality of two-dimensional images 380, according to MPS coordinate data 382, all of which are respective of a selected activity-state within the cycles of ECG data 384. The processor reconstructs three-dimensional image 106 from all the two-dimensional images which belong to of activity-state $T_2$. In addition, the processor generates trajectory 114 (FIG. 1B) of the catheter, which corresponds to activity-state $T_2$, from points 342, 344 and 346 (FIG. 6B). The processor superimposes trajectory 114 and real-time representation 112 (FIG. 1B) of a tip 390 of the catheter, on three-dimensional image 106.

A system (not shown) can playback the sequence of reconstructed images or a selected cycle of the originally acquired two-dimensional images, according to the stored ECG data or at predetermined time intervals. The system can also playback the sequence of reconstructed images or a selected cycle of the originally acquired two-dimensional images, in synchrony with real-time detected ECG data.

It is noted that since the catheter moves within lumen 108 in real-time, no synchronization is required with respect to the organ timing signal in that aspect. However, it is noted that the processor has to register the coordinate system in which the images were acquired, with the coordinate system of the MPS sensor of the catheter, or to use the same MPS system for the image acquisition process and the playback surgical procedure.

Following is a description of a GUI which allows the operator to freeze a three-dimensional image of a lumen, at a selected activity-state of an organ of the patient. The GUI also allows the operator to move forward and backward in terms of activity-state.

Figure 7:
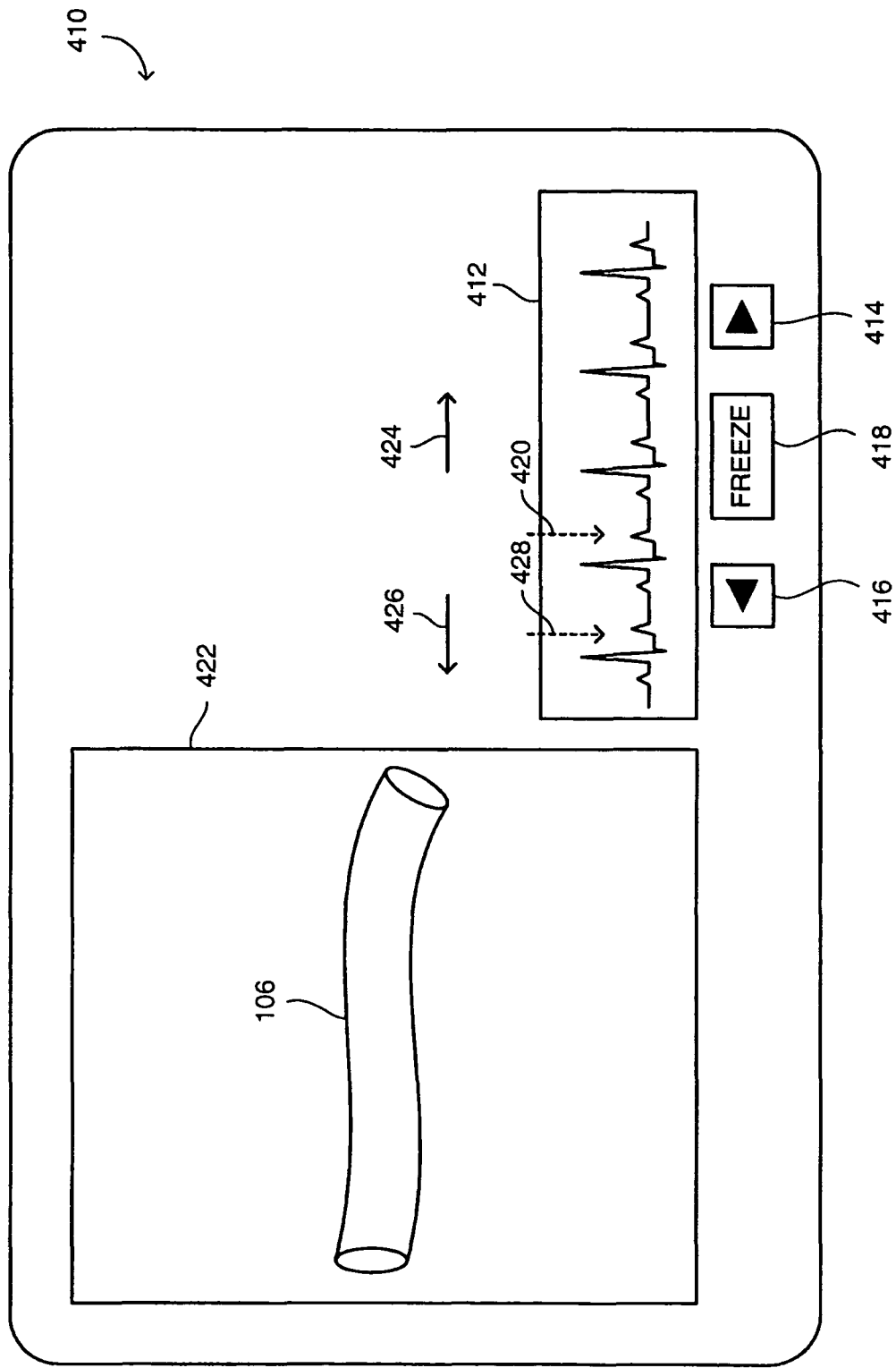
FIG. 7 is a schematic illustration of an ECG coordinated display (i.e., a GUI) of a lumen, constructed and operative in accordance with a further embodiment of the disclosed technique.

Reference is further made to FIG. 7, which is a schematic illustration of an ECG coordinated display (i.e., a GUI) of a lumen, generally referenced 410, constructed and operative in accordance with a further embodiment of the disclosed technique. ECG coordinated display 410 includes an ECG timing signal 412, a forward button 414, a backward button 416, a freeze button 418 and three-dimensional image 106 (FIG. 1B).

Three-dimensional image 106 corresponds with an activity-state 420 in ECG timing signal 412. When the operator presses forward button 414, a sequence of three-dimensional images of lumen 108 is displayed in a window 422. Each of the three-dimensional images displayed in window 422, corresponds with the respective activity-state in ECG timing signal 412, as if ECG timing signal 412 would advance in a direction designated by an arrow 424.

When the operator presses backward button 416, a sequence of three-dimensional images of lumen 108 is successively displayed in window 422. Each of the three-dimensional images displayed in window 422 corresponds with the respective activity-state in ECG timing signal 412, as if ECG timing signal 412 would retard in a direction designated by an arrow 426.

When the operator presses freeze button 418, a three-dimensional image of lumen 108 is displayed in window 422, wherein the three-dimensional image corresponds with a selected activity-state 428. In this manner the three-dimensional image of lumen 108 in window 422 remains stationary at activity-state 428, during which the physician can inspect the three-dimensional image of lumen 108.

Each of the three-dimensional images, which are displayed in window 422, is acquired by a system (not shown), during the scanning process. Thus, the operator can view animated three-dimensional images of lumen 108 as the heart of the patient would beat either forward or backward in time. The operator can alternatively view a three-dimensional image of lumen 108, which corresponds with a selected activity-state during a selected heart cycle of the patient, by pressing freeze button 418 at a selected point in time. It is noted that other sequenced images, such as a reference real-time image (i.e., served as road map during navigation, such as a fluoroscopic image, and the like) can also be made to freeze-up.

Following is a description of a GUI for identifying a plaque within the lumen, having a selected percentage of occlusion. According to an algorithm, the processor automatically designates the necessary marks on a real-time image of the lumen, as the selected position to which the medical device is to be delivered.

Figure 8A:
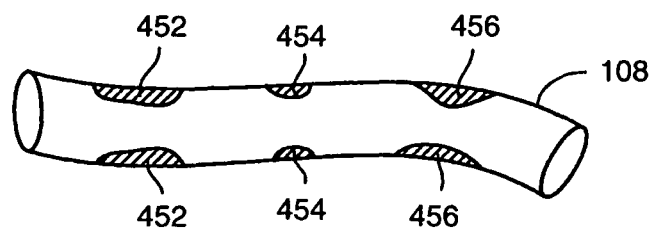
FIG. 8A is an illustration of the lumen of FIG. 1A, having a plurality of occluded regions.
Figure 8B:
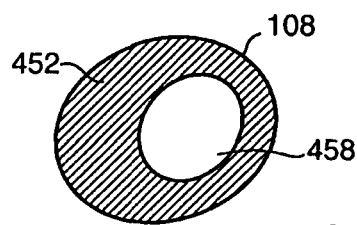
FIG. 8B is a cross-sectional view of a selected region of the lumen of FIG. 8A.
Figure 8C:
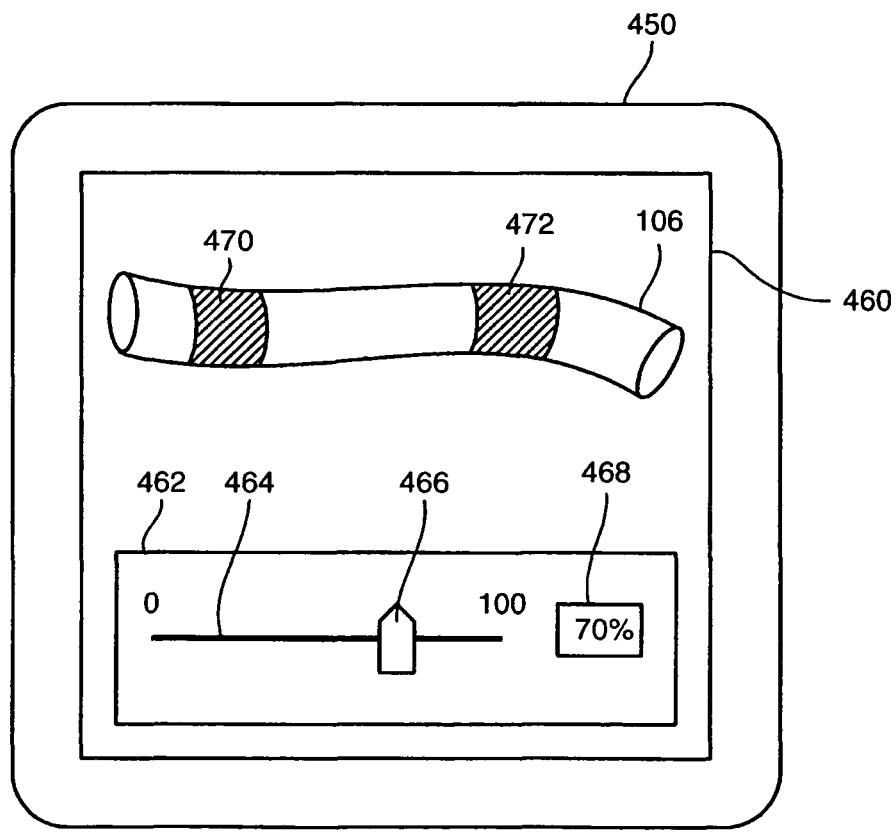
FIG. 8C is a schematic illustration of a representation of the lumen of FIG. 8B in a GUI, operative in accordance with another embodiment of the disclosed technique.

Reference is further made to FIGS. 8A, 8B and 8C. FIG. 8A is an illustration of the lumen of FIG. 1A, having a plurality of occluded regions. FIG. 8B is a cross-sectional view of a selected region of the lumen of FIG. 8A. FIG. 8C is a schematic illustration of a representation of the lumen of FIG. 8B in a GUI, generally referenced 450, operative in accordance with another embodiment of the disclosed technique.

Lumen 108 includes plaques 452, 454 and 456. It is noted that plaques 452, 454 and 456 can be fixed in their places or be dynamic. Plaques 452, 454 and 456 block lumen 108 by 75%, 60% and 80%, respectively. With reference to FIG. 8B, the hatched area denotes the blockage due to plaque 452 within lumen 108, leaving ducting 458 open for blood flow.

A processor (not shown) can determine the percentage of occlusion, according to a plurality of methods, taking into account parameters such as plaque type, plaque density, and the like. The following is a simple example for such a method:

$$\%_{BLOCKED} = \left(1 - \frac{S_{LUMEN}}{S_{ARTERY}}\right) \cdot 100$$

where, $S_{LUMEN}$ denotes the cross section of ducting 458 and $S_{ARTERY}$ denotes the total internal area of lumen 108.

GUI 450 includes a graphical window 460. Graphical window 460 includes three-dimensional image 106 and a ratio selection window 462. Ratio selection window 462 includes a graduation bar 464, a pointer 466 and a numerical box 468. The operator can dynamically set the occlusion percentage threshold, by dragging pointer 466 along graduation bar 464, via a user interface (not shown). Alternatively, the operator can enter a selected occlusion percentage threshold in numerical box 468, through the user interface. In the example set forth in FIG. 8B, the numerical value 70%, of the selected percentage is shown in numerical box 468.

A system (not shown) then marks only those regions on three-dimensional image 106, which are occluded more than the selected occlusion percentage. In the example set forth in FIG. 8B, only those regions of lumen 108 which are occluded 70% or more, are marked in three-dimensional image 106. Plaques 452 and 456, which exceed 70%, are represented by marked regions 470 and 472, respectively, on three-dimensional image 106. Marked regions 470 and 472 are differentiated from the rest of the portions of three-dimensional image 106, by being colored in a different hue, marked by hatches, animated, and the like.

It is noted the system enables the operator to manually correct the marking on screen, in case that the operator, according to her medical knowledge and experience detects for example, that the plaque portion should be different than what the system indicated. It is further noted that the system can present the various layers of the lumen (i.e., media, adventitia and intima), in GUI 450, in different colors.

Following is a description of a method for detecting the organ timing signal of the lumen, either due to the cardiac cycle or the respiratory cycle, by employing the MPS, instead of the ECG monitor. The term "time-tagging" herein below refers to the process of associating a data element, with the exact time at which that data element was obtained (e.g., associating an MPS coordinate reading with the exact time at which that reading was obtained). The data obtained via a plurality of MPS sensors (e.g., one attached to the tip of the catheter, one to the two-dimensional image acquisition device, one to the body of the patient, and one to an operation table) is time-tagged. It is noted, that in case a plurality of transmitters similar to transmitters 590A (FIG. 11), 590B, and 590C, as described herein below, are attached to the two-dimensional image acquisition device, there is no need to attach an MPS sensor to the two-dimensional image acquisition device. The reason in this case, is that the coordinate system of the two-dimensional image acquisition device is registered with that of the MPS. The two-dimensional images acquired by each two-dimensional image acquisition device (not shown) is also time-tagged. The time-tags are taken into account when processing the data elements stored in a database (not shown).

Latency compensation is performed on all the time-tagged data elements. In general, image frames from the set of two-dimensional (2D) images acquired by, the two-dimensional image acquisition device are shifted so that the time-tags thereof match the time-tag of the corresponding MPS data set (i.e., images acquired at the same time as an MPS coordinate reading was obtained will be matched with one another).

The term "corresponding data sets" herein below, refers to a pair of data sets which have the same time-tags. It is noted that the time-tag of a data set refers to the set of time-tags of the elements within the data set. For example, an MPS data set is corresponding with a two-dimensional images data set if readings in the MPS data set have the same time-tag as the images in the two-dimensional images data set.

Corresponding data sets represent data sets that occur during the same session in a medical procedure. The term "Non-corresponding data sets" herein below, refers to a pair of data sets which have different time-tags. For example, an MPS data set is non-corresponding with a two-dimensional images data set if the readings in the MPS data set have a different time-tag than all the images in the two-dimensional images data set. Non-corresponding data sets represent data sets that were recorded during different sessions (within the same or different medical procedures).

Figure 9:
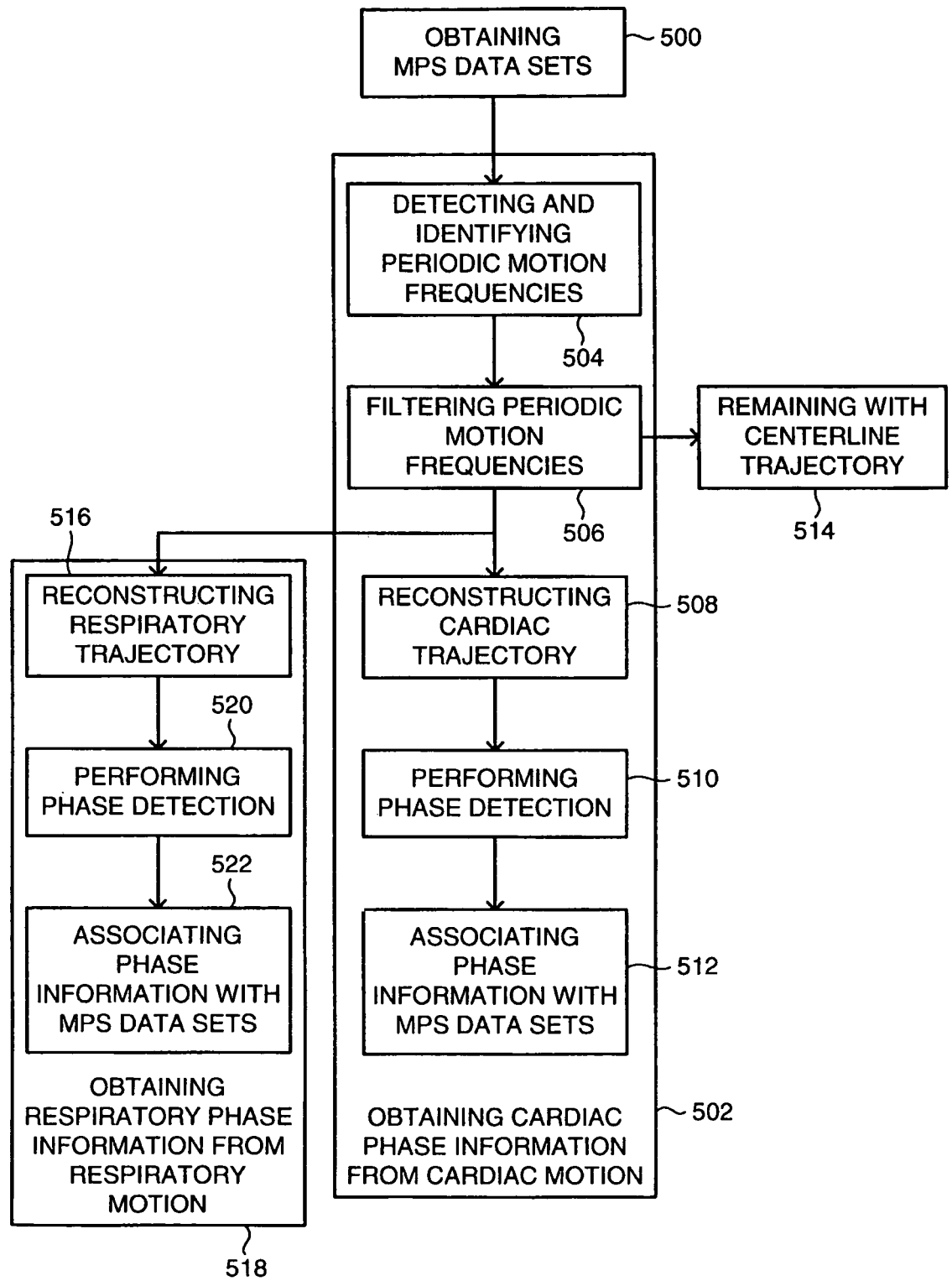
FIG. 9 is a schematic illustration of a method for determining an organ timing signal of an organ of the patient, according to position data of an MPS sensor which moves together with the movements of the organ, operative in accordance with a further embodiment of the disclosed technique.

Reference is further made to FIG. 9, which is a schematic illustration of a method for determining an organ timing signal of an organ of the patient, according to position data of an MPS sensor which moves together with the movements of the organ, operative in accordance with a further embodiment of the disclosed technique. In procedure 500, data sets are obtained from an MPS. Each data set includes a series of position coordinate readings of the two-dimensional image acquisition device, the catheter, a selected area of the body of the patient, or the operating table on which the patient is lying, respectively, as received from the respective MPS sensor.

The MPS processes detected electromagnetic fields to obtain the respective position coordinate readings, which are subsequently stored in the database. It is recalled that each MPS sensor position coordinate reading is time-tagged, or associated with the exact time at which the reading was obtained. Thus, each MPS data set, received from an MPS sensor, attached to the tip of the catheter, includes a collection of coordinate readings demonstrating the precise motion trajectory of the catheter over time.

In procedure 502, cardiac phase information is obtained from cardiac motion. In particular, cardiac phase information is obtained from data streams originating from the MPS sensor located on the catheter. Procedure 502 consists of procedures 504, 506, 508, 510 and 512.

In procedure 504, periodic motion frequencies are detected and identified in a time-tagged MPS data set. As the catheter is maneuvered within lumen 108, the motion of the catheter is influenced by two additional factors. The first factor relates to the activity of the heart, or cardiac motion, such as systole and diastole. Cardiac motion affects lumen 108 in a certain way, such as contraction or expansion in varying degrees and at periodic intervals. The second factor relates to the breathing activity, or respiratory motion, such as inhaling and exhaling. Respiratory motion affects lumen 108 in a certain way, such as contraction or expansion in varying degrees and at periodic intervals. Taken together, the overall motion of the catheter is composed of the cardiac motion and the respiratory motion superimposed onto the movement associated with maneuvering the catheter (which corresponds to the topography of the lumen system).

Since the cardiac motion and respiratory motion are cyclic in nature, the periodic frequencies can be detected in the overall trajectory of the catheter. The specific frequencies relating to the cardiac motion exhibit different characteristics than the specific frequencies relating to the respiratory motion. The specific frequencies relating to the cardiac motion are identified from the detected periodic frequencies. Similarly, the specific frequencies relating to the respiratory motion are identified from the detected periodic frequencies. The processor performs the analysis on the MPS data set and identifies the relevant periodic motion frequencies.

In procedure 506, periodic motion frequencies are filtered from the time-tagged MPS data set. The periodic motion frequencies detected in procedure 504 are separated out from the overall trajectory of the catheter. The remaining motion components correspond to the central axis of the maneuvers of the catheter, which represents the vessel topography, or "centerline trajectory" (referenced procedure 514). The time-tags associated with the MPS data set are retained for each of the filtered periodic motion frequencies. The processor filters out the relevant periodic motion frequencies from the MPS data set.

In procedure 508, the mechanical movement of lumen 108 due to the cardiac motion, or "cardiac trajectory", is reconstructed from the MPS data sets and from the filtered periodic motion frequencies. In particular, the cardiac trajectory is reconstructed according to the previously identified specific frequencies relating to the cardiac motion. The reconstructed cardiac trajectory may be reflected, for example, by a graph that indicates the trajectory of lumen 108 due to cardiac motion over a period of time. The processor analyzes the relevant periodic motion frequencies and creates a reconstruction of the cardiac trajectory.

In procedure 516, the mechanical movement of lumen 108 due to the respiratory motion, or "respiratory trajectory", is reconstructed from the MPS data sets and the filtered periodic motion frequencies. In particular, the respiratory trajectory is reconstructed according to the previously identified specific frequencies relating to the respiratory motion. The reconstructed respiratory trajectory may be reflected, for example, by a graph that indicates the trajectory of lumen 108 due to respiratory motion over a period of time. The processor analyzes the relevant periodic motion frequencies and creates a reconstruction of the respiratory trajectory.

Reconstruction of the respiratory trajectory may be based solely on coordinate readings obtained from the external reference sensors (i.e., MPS sensors attached to the body of the patient and to the operation table). It is noted that an additional reference sensor (or plurality thereof) may be attached (i.e., externally or internally) to the body of the patient, to monitor breathing patterns, and the like. For example, an intravascular sensor may be used for this purpose.

This sensor functions as a confirmation mechanism to provide supporting data regarding respiratory motion, and more accurately determine periodic motion frequencies relating to respiratory motion. It is noted that the same or an additional sensor (or plurality thereof) may be used for gathering additional cardiac data either as a confirmation mechanism or for providing supporting data for cardiac phase detection.

In procedure 510, phase detection is performed on the reconstructed cardiac trajectory. The cardiac trajectory consists of different phases or activity-states of the heart, corresponding to different points within a cardiac cycle. The phases repeat themselves periodically with each cycle. The plurality of cardiac activity-states is identified on the reconstructed cardiac trajectory during phase detection. The processor performs the analysis of the cardiac trajectory and identifies the different cardiac cycle phases.

Reference is further made to FIG. 10A, which is a schematic illustration of a cardiac trajectory, in an electrical signal representation and in a mechanical signal representation. The mechanical signal representation of the cardiac trajectory, generally referenced 550, includes a plurality of cardiac activity-states (i.e., cardiac cycle phases), such as activity-states $T_1$, $T_2$ and $T_3$, in each of a plurality of cardiac cycles 552, 554 and 556. The mechanical representation of the cardiac trajectory is equivalent to the cardiac trajectory reconstructed from the MPS data sets and the filtered periodic motion frequencies (procedures 506 and 508). The electrical signal representation of the cardiac trajectory, generally referenced 558, depicts the same activity-states $T_1$, $T_2$ and $T_3$, in each of cardiac cycles 552, 554 and 556.

However the precise time at which these activity-states occur may be different in the two representations, as there is a slight delay at the electrical representation with respect to the mechanical representation. For example, it is shown that activity-state $T_3$ of cardiac cycle 554 occurs a at time $t_A$ in cardiac trajectory 550 and at a time $t_B$ in cardiac trajectory 558. Therefore, it is necessary to perform an alignment between the activity-states, when using information from the electrical representation for phase detection. The electrical representation 558 of the cardiac trajectory is equivalent to the electrical timing signals obtained by an ECG monitor (not shown).

It is noted that the detection of cardiac phases is performed based solely on data sets originating from at least an MPS sensor attached to the catheter, and perhaps also from the reference sensors attached to the body of the patient and the operation table. These data sets provide a mechanical representation of the cardiac trajectory. No external monitoring device is required to obtain cardiac phase information.

It is noted that periodic motion components relating to the respiratory motion may also be used as supporting data for cardiac phase detection. It is further noted that phase detection may be performed on the original MPS data sets, rather than on the reconstructed cardiac trajectory, using the detected and filtered periodic motion frequencies. The different phases or activity-states of the heart are identified directly on the MPS data sets obtained in procedure 500.

In procedure 512, cardiac phase information is associated with the MPS data sets. Each data set obtained from an MPS sensor attached to the catheter, relating to the position of the catheter is matched to one of a plurality of activity-states $T_1$, $T_2$ and $T_3$, according to their corresponding time elements (i.e., time-tags). The position of lumen 108, and consequently the position of the catheter, is different during different activity-states of lumen 108. The processor associates between a coordinate reading and the matching phase thereof, and stores the information in the database.

Respiratory phase information may be obtained from the respiratory motion, in a similar manner as cardiac phase information is obtained from the cardiac motion. Respiration activity-states may be identified on the reconstructed respiratory trajectory using the periodic motion components relating to the respiratory motion. Periodic motion components relating to the respiratory motion may also be used in correlation with non-corresponding data sets.

Respiratory phase information is obtained from respiratory motion in an optional procedure 518. Procedure 518 consists of procedures 516, 520 and 522. In procedure 516, a respiratory trajectory is reconstructed from the MPS data sets and the filtered periodic motion frequencies, as described herein above in connection with procedures 504, 506 and 508.

In procedure 520, phase detection is performed on the reconstructed respiratory trajectory. Like the cardiac trajectory, the respiratory trajectory consists of different phases or activity-states of the lungs, corresponding to different points within a respiratory cycle. The respiratory activity-states of the lungs can be identified from the phases of the respiratory trajectory. The phases repeat themselves periodically with each cycle. The respiratory activity-states are identified on the reconstructed respiratory trajectory during phase detection. The processor performs the analysis of the respiratory trajectory and identifies the different respiratory cycle phases.

Figure 10B:
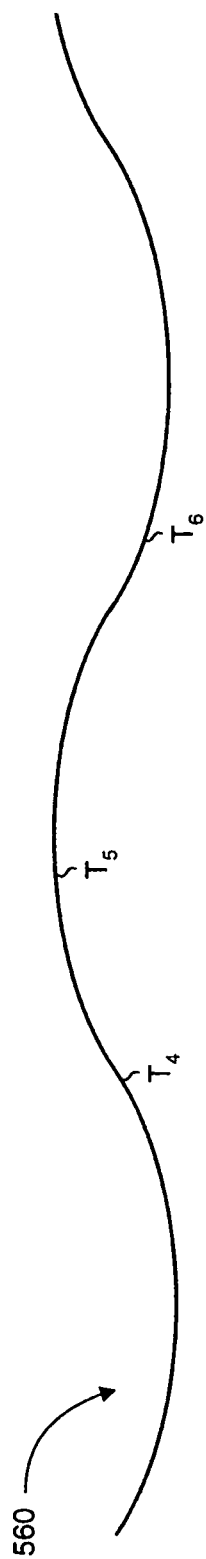
FIG. 10B is a schematic illustration of a respiratory trajectory in a mechanical signal representation.

Reference is further made to FIG. 10B, which is a schematic illustration of a respiratory trajectory in a mechanical signal representation, generally referenced 560. Mechanical signal representation 560 includes a plurality of respiratory activity-states (i.e., respiratory cycle phases), such as activity-states $T_4$, $T_5$ and $T_6$. Mechanical representation 560 is equivalent to the respiratory trajectory reconstructed from the MPS data sets, and the filtered periodic motion frequencies in procedure 508.

It is noted that the detection of respiratory phases is performed based solely on data sets detected by an MPS sensor attached to the catheter, and from MPS sensors attached to the body of the patient and to the operation table. These data sets provide a mechanical representation of the respiratory trajectory. No external monitoring device is required to obtain respiratory phase information. It is further noted that phase detection may be performed on the original MPS data sets, rather than on the reconstructed respiratory trajectory, using the detected and filtered periodic motion frequencies. The different phases or activity-states of the lungs are identified directly on the MPS data sets obtained in procedure 500.

It is noted that the actual value of the cardiac rate or respiratory rate of the patient may be obtained without using any external monitoring device (such as an ECG monitor—not shown). The cardiac rate or respiratory rate of the patient can be obtained solely from the MPS sensors attached to the catheter, the body of the patient and to the operation table, either individually or jointly.

In procedure 522, respiratory phase information is associated with the MPS data sets. Each data set obtained from the MPS sensor attached to the catheter, is matched to one of activity-states $T_4$, $T_5$ and $T_6$, according to their corresponding time-tags. Procedure 522 is analogous to procedure 512 discussed herein above.

Following is a description of automatic maneuvering of the catheter within lumen 108 (FIG. 1A). The term "topological representation" herein below, refers to a mapping of a lumen system (e.g., the circulation, the bronchial tree, the urogenital system, the renal system) of the body of the patient, which a system according to the disclosed technique employs, in order to maneuver the catheter from an origin to a destination. The mapping can be either two-dimensional or three-dimensional. Alternatively, it is noted that the term "topological representation" may include just the path to be followed in the lumen system.

Figure 11:
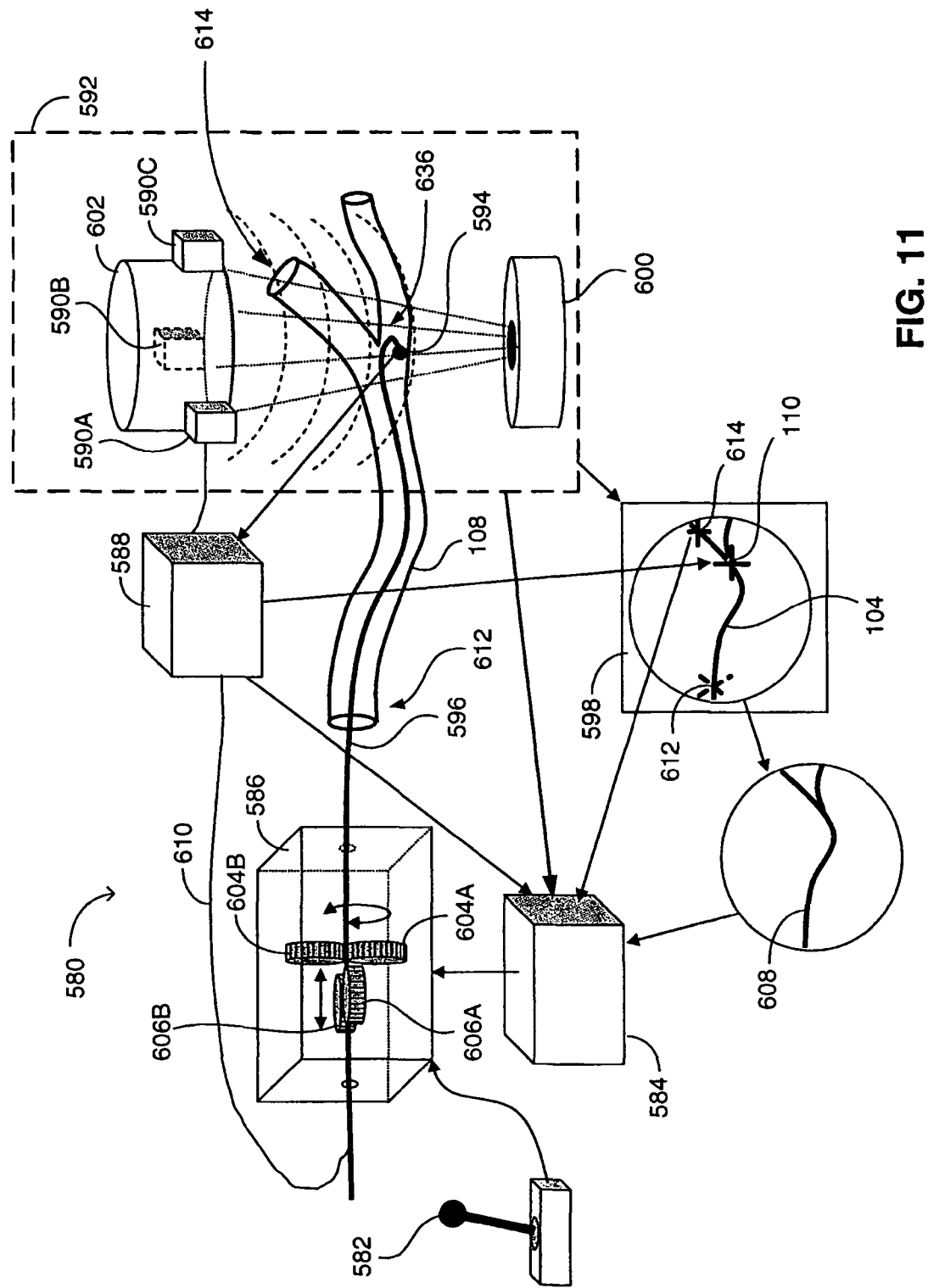
FIG. 11 is a schematic illustration of a system for automatically maneuvering a catheter within a lumen of the body of a patient, constructed and operative in accordance with another embodiment of the disclosed technique.
Figure 12:
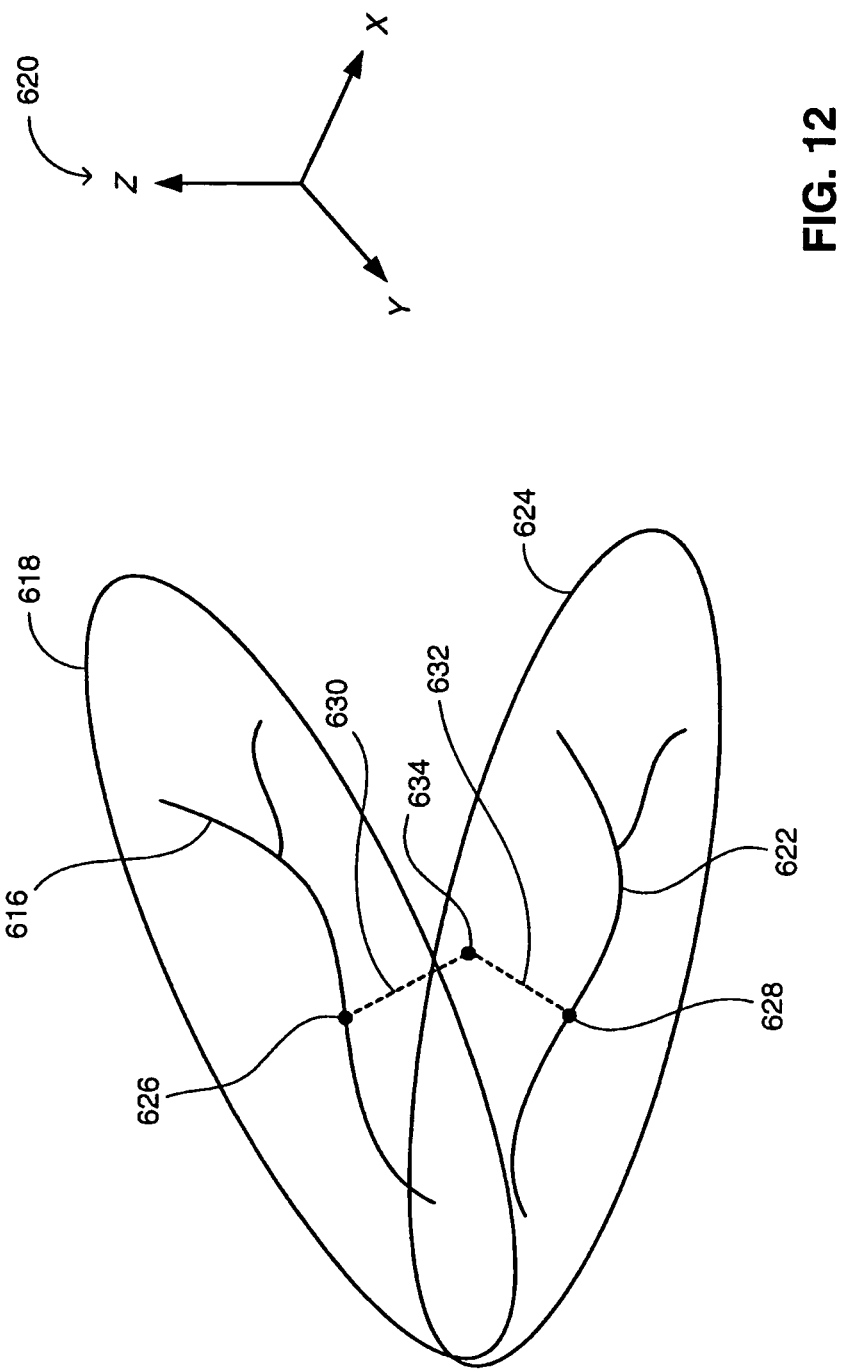
FIG. 12 is a schematic illustration of a method by which the imaging system of the system of FIG. 11 determines the coordinates of a path within the lumen, in three dimensions.

Reference is further made to FIGS. 11 and 12. FIG. 11 is a schematic illustration of a system, generally referenced 580, for automatically maneuvering a catheter within a lumen of the body of a patient, constructed and operative in accordance with another embodiment of the disclosed technique. FIG. 12 is a schematic illustration of a method by which the imaging system of the system of FIG. 11 determines the coordinates of a path within the lumen, in three dimensions.

With reference to FIG. 11, system 580 includes a joystick 582, a controller 584, a moving mechanism 586, an MPS 588, a plurality of transmitters 590A, 590B and 590C, an imaging system 592, a MPS sensor 594, a catheter 596 and a display 598. Imaging system 592 includes a radiation generator 600 and a radiation detector 602. Imaging system 592 can be an X-ray system, fluoroscope, C-arm imager, CT, PET, ultrasound system, MRI, and the like.

Moving mechanism 586 can include a pair of angular movement rollers 604A and 604B, and a pair of linear movement rollers 606A and 606B, and respective moving elements (not shown) such as electric motors, actuators, and the like. However, moving mechanism 586 can include other, alternative or additional elements, as long as it imparts to catheter 596 the necessary motions described herein below (e.g., piezoelectric motors which transfer linear movement through friction). Optionally, moving mechanism 586 can be disposable in order to keep it sterile. Controller 584 includes a processor (not shown) and a storage unit (not shown) for storing information respective of a path 608, which catheter 596 should move according to, within lumen 108 (FIG. 1A).

Moving mechanism 586 is coupled with joystick 582 and with controller 584. Controller 584 is coupled with imaging system 592. MPS 588 is coupled with controller 584 and with transmitters 590A, 590B and 590C. MPS sensor 594 is coupled with MPS 588 by a conductor 610 (i.e., a conductive coupling). Display 598 is coupled with MPS 588 and with imaging system 592. MPS sensor 594 is located at a distal portion of catheter 596.

During the medical operation, the body of the patient (not shown) is located between radiation generator 600 and radiation detector 602. Imaging system 592 has at least one degree of freedom, thereby being able to take a plurality of images of the body of the patient, from different directions. Imaging system 592 provides a signal to display 598, respective of two-dimensional image 104 (FIG. 1A), for display 598 to display two-dimensional image 104.

Path 608 is a three-dimensional curve between an origin 612 and a destination 614 of a distal portion (not shown) of catheter 596 relative to lumen 108. Both origin 612 and destination 614 are within a field of view of imaging system 592. Path 608 is determined during an imaging session prior to the medical operation, and stored in the storage unit.

Controller 584 calculates and constructs path 608, for example, according to a plurality of two-dimensional images obtained from lumen 108, with the aid of a C-arm imager. For example, the C-arm can obtain two two-dimensional ECG gated images of lumen 108 at two different non-parallel ECG gated image planes. When the operator indicates origin 612 and destination 614, the C-arm constructs path 608 in three dimensions. It is noted that controller 584 calculates path 608 based on one or more image processing algorithms, according to contrast variations of lumen 108 relative to the background.

With further reference to FIG. 12, imaging system 592 captures an image 616 of lumen 108 on an image plane 618 in a three-dimensional coordinate system 620, and another image 622 of lumen 108 on an image plane 624 in three-dimensional coordinate system 620. Imaging system 592 is aware of the orientation between image planes 618 and 624 (i.e., the angles there between). Imaging system 592 identifies a feature 626 of lumen 108 in image 616 and a corresponding feature 628 in image 622. Imaging system 592 determines the three-dimensional coordinates of feature 626 (or feature 628) in three-dimensional coordinate system 620, by determining the intersection of normals 630 and 632 from features 626 and 628, respectively, to image planes 618 and 624, respectively, at a point 634. Imaging system 592 performs the above procedure for other features of lumen 108, thereby constructing path 608 in three dimensions.

A two-dimensional image which the C-arm obtains from the body of the patient, can include other lumens (not shown) in addition to lumen 108, which are located at planes different than the plane of lumen 108 (i.e., these additional lumens overlap lumen 108 in the captured image). In this case, when the operator indicates origin 612 and destination 614, it is not evident to the C-arm that the operator is interested in a path through lumen 108, and the C-arm can construct a path (not shown), which passes through another lumen which in the two-dimensional image overlaps lumen 108. Hence, the C-arm obtains another two-dimensional image of lumen 108 at another image plane, such that in the new two-dimensional image, lumen 108 is not overlapped by any other lumens.

Prior to the medical operation, the coordinate systems of MPS 588 and imaging system 592 are set to a common two-dimensional coordinate system, for display 598 to superimpose real-time representation 110 (FIG. 1A) of MPS sensor 594, on two-dimensional image 104, during the medical operation. This method is described herein above in connection with FIG. 6C. The information displayed by display 598, serves the physical staff to observe the location of the distal portion of catheter 596 relative to lumen 108, throughout the medical operation. This two-dimensional coordinate system can be determined for example, according to the following method.

A first transformation model between the three-dimensional coordinate system of MPS 588 and the three-dimensional coordinate system of imaging system 592 is determined. A second transformation model between the three-dimensional coordinate system of imaging system 592 and a two-dimensional coordinate system of imaging system 592 is determined. The three-dimensional coordinate system of MPS 588 is transformed to the three-dimensional coordinate system of imaging system 592, by applying the first transformation model to the three-dimensional coordinate system of MPS 588. The three-dimensional transformed coordinate system of imaging system 592 is transformed to the two-dimensional coordinate system of imaging system 592, by applying the second transformation model to the three-dimensional transformed coordinate system of imaging system 592.

The first transformation model is determined according to a set of points in the three-dimensional coordinate system of MPS 588 and another set of points in the three-dimensional coordinate system of imaging system 592. The second transformation model is determined according to external parameters of imaging system 592 (i.e., a set of points in the three-dimensional coordinate system of imaging system 592) and internal parameters of imaging system 592 (e.g., lens angle, focal length, magnification).

Following is a description of operation of system 580, for performing an operation on the vessels in the neck region of a patient. In this case, path 608 is a three-dimensional curve within the axillary artery (represented by lumen 108) which marks a path from the region of the first rib (i.e., origin 612) to the thyrocervical trunk (i.e., destination 614). At the stage of medical operation, the physical staff inserts catheter 596 to the body of the patient through the right brachial artery (not shown), and manually maneuvers catheter 596 to reach origin 612.

At this point, system 580 takes over, to automatically maneuver catheter 596 to destination 614. In response to the electromagnetic field produced by transmitters 590A, 590B and 590C, MPS sensor 594 sends a signal to MPS 588 via conductor 610, respective of the three-dimensional position of MPS sensor 594. Alternatively, MPS sensor 594 is coupled with MPS 588 wirelessly and without conductor 610, in which case MPS sensor 594 sends this position signal to MPS 588 wirelessly.

MPS 588 determines the coordinates of MPS sensor 594 according to the signal received from MPS sensor 594. MPS 588 sends a signal respective of the coordinates of MPS sensor 594 to controller 584, in the three-dimensional coordinate system of MPS 588. MPS 588 sends a signal respective of the coordinates of MPS sensor 594 to display 598, in the two-dimensional coordinate system of imaging system 592, as described herein above.

Throughout the medical operation, display 598 displays two-dimensional image 104 of an operational region of lumen 108 (i.e., a section between origin 612 and destination 614) according to a signal received from imaging system 592. Display 598 also displays representation 110 of the current location of MPS sensor 594 (i.e., the distal portion of catheter 596), superposed on two-dimensional image 104, according to the signal received from MPS 588. Alternatively, the current location of the MPS sensor can be superposed on a three-dimensional image of the lumen (e.g., the coronary tree).

Instead of path 608, the controller can employ a topographical representation of the lumen system of the patient, in order to control the moving mechanism to maneuver the catheter through the lumen system, from an origin to a destination within the lumen system. In this case, the controller determines the best path for the catheter to reach the destination. It is noted that the controller may change the path in real-time, depending on findings during the navigation process (e.g., blocked passages, lumen which is narrower than expected). The controller modifies the path according to the feedback provided in real time by the MPS sensor, and by comparing the actual position and orientation of the MPS sensor with the expected position and orientation. Furthermore, the controller modifies a predefined three-dimensional path which is used as a three-dimensional roadmap for the planning process.

The system can further include a processor (not shown) coupled with the MPS and with the display, and an organ monitor (not shown) such as an ECG coupled with the processor. The organ monitor monitors the organ timing signal of a monitored organ and sends a respective signal to the processor. The processor sends a video signal to the display respective of an image of the lumen, corresponding with the current activity-state of the monitored organ detected by the organ monitor. The display displays an image of the lumen, according to the current activity-state. Thus, the display displays a superposition of a representation of the MPS sensor on a reconstructed image of the lumen, taking into account the movements of the lumen due to the timing signal of the monitored organ (e.g., the heart beat of the patient). The display can display a three-dimensional reconstructed image of the lumen. This three-dimensional reconstructed image is displayed relative to the coordinate system of the body of the patient.

Alternatively, the medical positioning system can filter out the organ timing signal (i.e., producing a filtered MPS reading) and the current position of the MPS sensor in the coordinate system of the lumen, from a multitude of positions of the MPS sensor, in the coordinate system of the body of the patient. In this case, the controller updates the topological representation and the position of the tip of the catheter according to the filtered MPS reading. The controller controls the moving mechanism according to the updated topological representation and the updated position of the catheter. Furthermore, the display can display the updated topological representation and the updated representation of the distal portion of the catheter, superposed on a substantially stationary three-dimensional reconstructed image of the lumen.

Moving mechanism 586 operates according to the commands received from controller 584, to maneuver catheter 596 along path 608, from origin 612 to destination 614. For this purpose, the pair of angular movement rollers 604A and 604B twist catheter 596 clockwise and counterclockwise relative to the longitudinal axis (not shown) of catheter 596, and the pair of linear movement rollers 606A and 606B move catheter 596 forward and backward. Controller 584 constantly receives a signal from MPS 588 respective of three-dimensional coordinates of MPS sensor 594 at any given time (i.e., a feedback), thereby allowing moving mechanism 586 to apply corrections to possible errors of movement along path 608. These corrections are applied in the following manner.

Controller 584 sends a signal at predetermined time increments to moving mechanism 586, to advance catheter 596 by a predetermined displacement increment. Controller 584 determines the advancement of the distal portion of catheter 596 at each time increment (according to the position signal received from MPS 588), and checks whether this advancement substantially matches the predetermined displacement by which catheter 596 was supposed to advance. In case the actual detected advancement does not match the predetermined displacement increment, controller 584 determines that catheter 596 has made contact with an obstacle (not shown) which prevents catheter 596 to advance according to path 608 (e.g., the distal portion of catheter 596 can be stuck at a bifurcation 636).

In this case, controller 584 sends a signal to moving mechanism 586 to retreat catheter 596 by a selected increment backward within lumen 108, and also to twist the distal portion of catheter 596 by a selected amount. After this twist, controller 584 sends a signal to moving mechanism 586 to advance catheter 596 by a predetermined displacement increment. Thus, moving mechanism 586 can maneuver catheter 596 to overcome the obstacle and to enter the predetermined branch (in this case the thyrocervical trunk at bifurcation 636).

It is noted that due to the three-dimensional position information which controller 584 receives as a real time feedback from MPS 588, controller 584 can control the operation of moving mechanism 586 to maneuver catheter 596 in three-dimensions. Thus, system 580 provides an advantage over systems in the prior art, in which the physical staff can maneuver the catheter according to a two-dimensional display, only in two dimensions. System 580 provides automatic maneuvering of catheter 596 through lumen 108 in three dimensions, while performing feedback oriented real time corrections in order to reach destination 614 within lumen 108.

Imaging system 592 (e.g., a C-arm) can detect lumen 108 from different directions in order to provide the information necessary for display 598 to display two-dimensional image 104. Imaging system 592 selects the one specific imaging direction at which the average distance of path 608 from an image plane (not shown), is minimal. If $X_i$ is the distance from a point i on path 608 normal to the image plane, where i=1,2,3 ... N, then the minimum average distance is, $$\min \frac{\sum_{1}^{N} x_i}{N} \quad (1)$$

In case path 608 follows many curves in space and deviates significantly from a two-dimensional path, then imaging system 592 can divide path 608 to different parts, and prepare the information for two-dimensional image 104, by selecting a different image plane for each part, while satisfying Equation 1.

It is noted that more than one MPS sensor can be located at the distal portion of the catheter. This arrangement is crucial in case the distal portion of the catheter is provided with a "curve-back" functionality. The "curve-back" movement can be provided for example, by employing Electro Active Polymers (EAP). The moving mechanism is likewise provided with the necessary elements to apply an appropriate torque to the distal portion of the catheter, to bend the distal portion. Moreover, with the aid of multiple MPS sensors, the display can display the current geometry of the distal portion.

Furthermore, the controller can obtain a more complete information respective of the geometry of the distal portion of the catheter, when the catheter is blocked by an obstacle, and thus expedite the maneuvering operation. For example, if the controller detects that the distal portion of the catheter has unexpectedly bent, then the controller determines that the tip of the catheter has made contact with an obstacle in the lumen. The controller can reach this conclusion for example, by comparing the detected orientation of the MPS sensor at a given point within the lumen, with the computed slope of the path at the same point within the lumen. In case the detected orientation and the computed slope do not match, the controller determines that the catheter has met an obstacle, thereby directing the moving mechanism to operate in order to move the catheter back from the obstacle.

In case the physical staff is unsatisfied with the automatic operation of moving mechanism 586, he can override controller 584, and manually operate moving mechanism 586 via joystick 582. The operator can intervene in any phase of operation of system 580, using joystick 582. This is a semi-automatic mode of operation of system 580, wherein controller 584 enables moving mechanism 586 to maneuver catheter 596 through the trivial portions of path 608, and the operator takes control of system 580 in the more intricate portions of path 608. In case of manual intervention, joystick 582 overcomes any automated action. It is noted that both in the automatic mode and the manual mode, the operator receives a visual feedback of the advancement of catheter 596 within lumen 108, by viewing representation 110 of the tip of catheter 596 on display 598.

According to another aspect of the disclosed technique, the processor produces a superimposed image which includes a superposition of a representation of the selected position within the lumen, on a real-time image of the lumen. The real-time image includes an image of the catheter and the medical device within the lumen, in real-time. With the aid of the superimposed image, the operator can visually maneuver the catheter which includes the medical device at the tip thereof, within the lumen, toward the selected position.

Figure 14B:
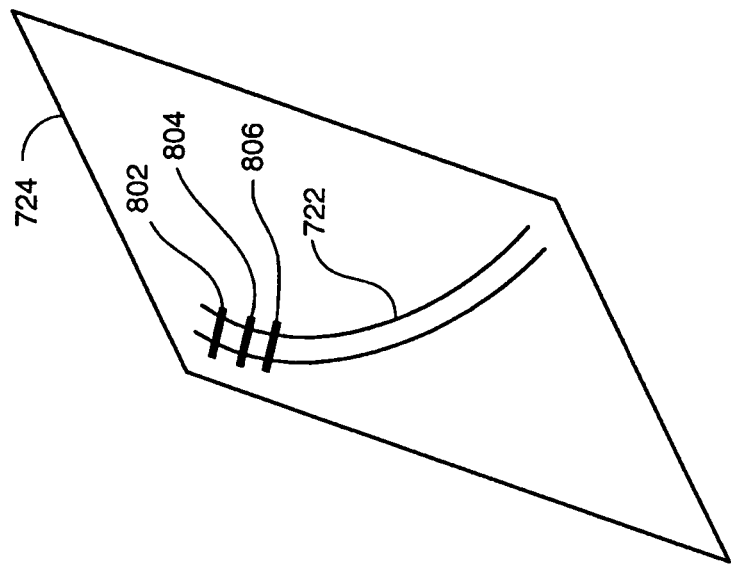
FIG. 14B is a schematic illustration of a second image of the lumen of FIG. 13, acquired by the image acquisition device of the system of FIG. 13, from a second viewing direction, at the marking stage.
Figure 14A:
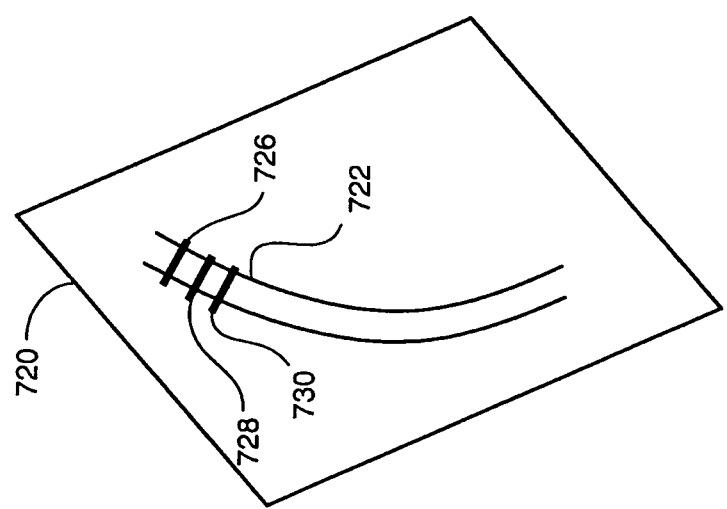
FIG. 14A is a schematic illustration of a first image of a lumen of the body of the patient of FIG. 13, acquired by the image acquisition device of the system of FIG. 13, from a first viewing direction, at a marking stage.

Reference is now made to FIGS. 13, 14A, and 14B. FIG. 13 is a schematic illustration of a system generally referenced 660, constructed and operative in accordance with a further embodiment of the disclosed technique. FIG. 14A is a schematic illustration of a first image of a lumen of the body of the patient of FIG. 13, acquired by the image acquisition device of the system of FIG. 13, from a first viewing direction, at a marking stage. FIG. 14B is a schematic illustration of a second image of the lumen of FIG. 13, acquired by the image acquisition device of the system of FIG. 13, from a second viewing direction, at the marking stage.

With reference to FIG. 13, system 660 includes an image acquisition device 662, a user interface 664, a processor 666, a display 668, a medical positioning system (MPS) 670, a transmitter 672, and MPS sensors 674 and 676. Image acquisition device 662 includes a structural member 678, a moving mechanism 680, an emitter 682, and an image detector 684. Processor 666 is coupled with user interface 664, display 668, and with MPS 670. MPS 670 is coupled with transmitter 672 and with MPS sensors 674 and 676. Moving mechanism 680, emitter 682, and image detector 684 are coupled with structural member 678.

MPS sensor 674 is firmly attached to the body of a patient 686 who is lying on a bed 688. MPS sensor 676 is firmly attached to image acquisition device 662. Each of MPS sensors 674 and 676 responds to electromagnetic radiations which transmitter 672 emits. MPS 670 determines the position of the body of patient 686, and the position of image acquisition device 662, according to an output of MPS sensors 674 and 676, respectively. Therefore, all movements of image acquisition device 662 and of the body of patient 686, are defined in a three-dimensional coordinate system respective of MPS 670. In case image acquisition device 662 is registered with MPS 670, MPS sensor 676 can be eliminated from system 660. Instead of MPS 670, other position detection systems can be employed to define the movements of the body of patient 686 and of image acquisition device 662, such as optical, acoustic, and the like.

Emitter 682 is located above the body of patient 686. Image detector 684 is located below the body of patient 686. Moving mechanism 680 enables structural member 678 to rotate about an axis (not shown) substantially parallel with a longitudinal axis (not shown) of bed 688, in directions referenced by arrows 690 and 692. In the example set forth in FIG. 13, image acquisition device 662 is a C-arm X-ray device. 30 However, it is noted that the image acquisition device can be a computer tomography (CT) device, a magnetic resonance imager (MRI), positron emission tomography (PET), single photon emission computer tomography (SPECT), ultrasound image detector, infrared image detector, X-ray imager, optical coherent tomography detector (OCT), and the like. User interface 664 can be tactile (e.g., keyboard, mouse, track-ball, touch-screen), acoustic (e.g., microphone, speaker), haptic (e.g., force-feedback joystick), and the like.

With further reference to FIG. 14A, image acquisition device 662 acquires an image 720 of a lumen 722 of the body of patient 686 from a first viewing direction. With reference to FIG. 14B, image acquisition device 662 acquires an image 724 of lumen 722, from a second viewing direction. Image 720 is a projection of a volume (i.e., a region of interest of the body of patient 686), on a first plane (not shown). Image 724 is a projection of the same volume on a second plane (not shown).

An operator (not shown) inputs position data respective of the selected position, by designating marks 726, 728, and 730, on image 720, to processor 666, via user interface 664. Marks 726, 728, and 730 designate the selected position within lumen 722 toward which a medical device (not shown), is to be maneuvered. The medical device is located at the tip of a catheter 732 (FIG. 13). For example, mark 726 designates the position at which a front end of a stent (not shown), should be placed, mark 730 designates the position at which the rear end of the stent should be placed, and mark 728 designates the position at which the middle of, the stent should be placed. The operator inputs position data respective of the same selected position, by designating marks 802 (FIG. 14B), 804, and 806, on image 724, to processor 666, via user interface 664.

The selected position defined by each of marks 726, 728, 730, 802, 804, and 806 is associated with only two coordinates in the three-dimensional coordinate system. Processor 666 determines the third coordinate of the selected position, in the three-dimensional coordinate system, according to the two-dimensional coordinates of each of corresponding ones of marks 726, 728, 730, 802, 804, and 806. Processor 666 for example, determines the coordinates of a mark 808 (FIG. 15A) according to the coordinates of marks 726 and 802, of a mark 810 according to the coordinates of marks 728 and 804, and of a mark 812 according to the coordinates of marks 730 and 806.

According to another embodiment of the disclosed technique, the image acquisition device acquires an image (not shown) of the lumen along a plane whose coordinates are defined in the three-dimensional coordinate system (e.g., an ultrasound image). In this case, it is sufficient for the operator to designate the marks only once on the image, since all three coordinates of each of the marks, are defined in the three-dimensional coordinate system.

According to another embodiment of the disclosed technique, the image acquisition device acquires a three-dimensional image of the lumen (e.g., in case of CT, MRI, PET, SPECT). In this case it is sufficient for the operator to mark the selected position only once on the three-dimensional image, since all slices of the three-dimensional image are defined in the three-dimensional coordinate system. Alternatively, display 668 displays a stereoscopic image of the lumen, in which case it is sufficient for the operator to mark the selected position only once on the stereoscopic image.

Figure 15B:
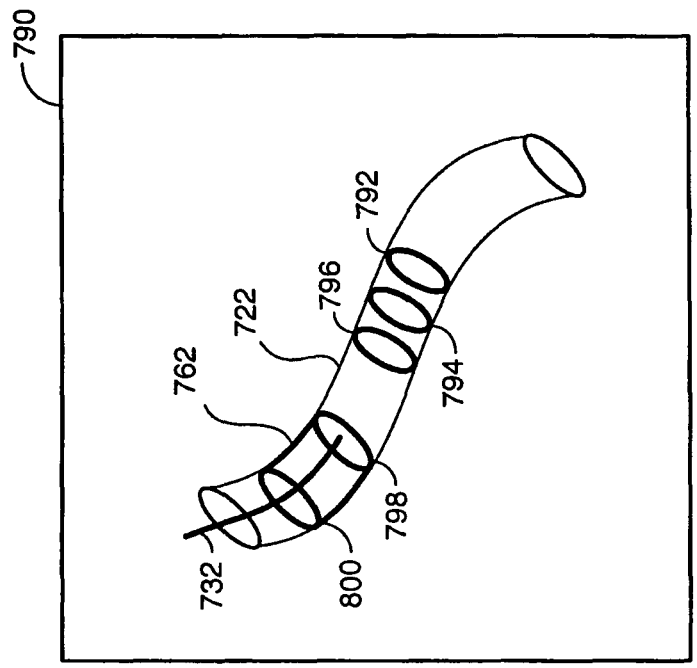
FIG. 15B is a schematic illustration of a real-time three-dimensional image of the lumen, during automatic maneuvering of the catheter toward the selected position within the lumen.
Figure 15A:
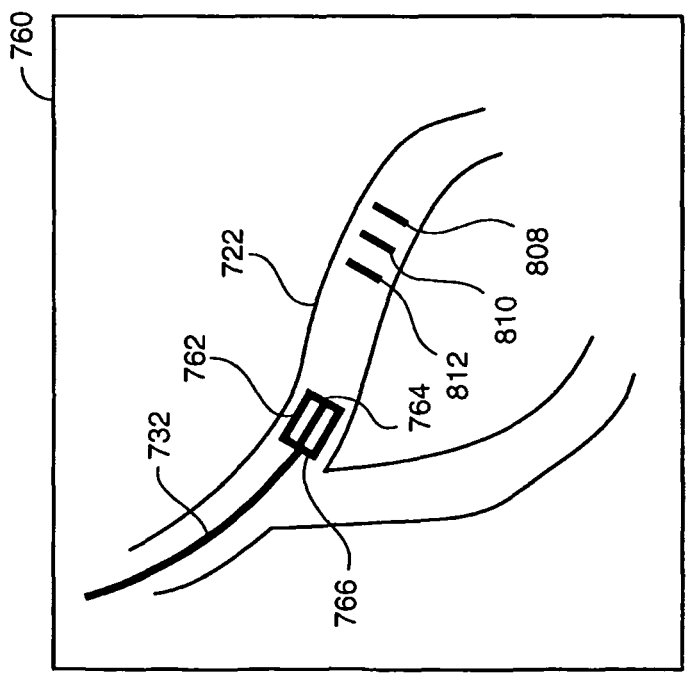
FIG. 15A is a schematic illustration of a real-time two-dimensional image of the lumen of the patient of FIG. 13, during visual maneuvering of the catheter of FIG. 13, toward a selected position within the lumen.
Figure 16B:
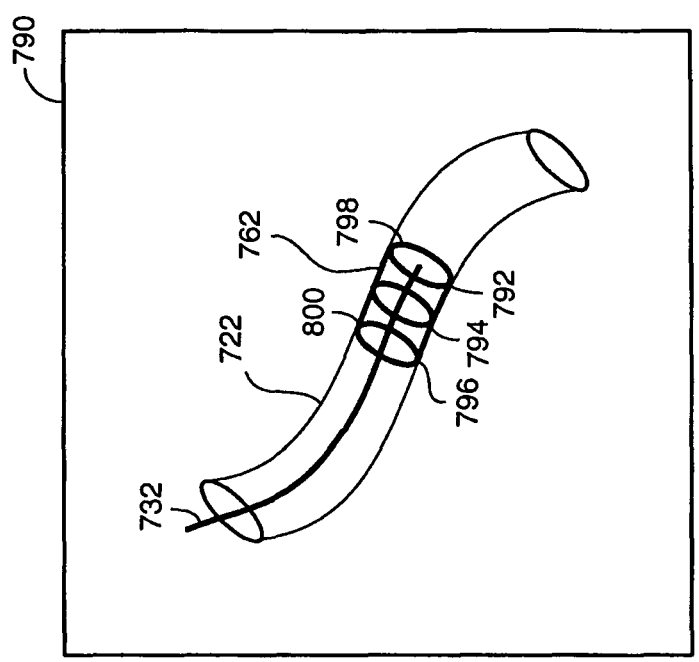
FIG. 16B is a schematic illustration of the lumen of FIG. 15B, when the medical device has reached the selected position.
Figure 16A:
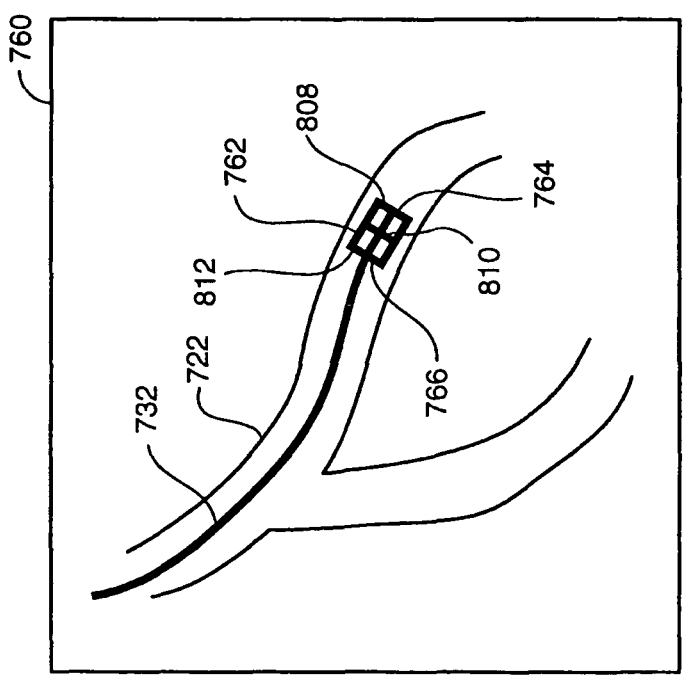
FIG. 16A is a schematic illustration of the lumen of FIG. 15A, when the medical device located at tip of the catheter, has reached the selected position.

Reference is now made to FIGS. 15A, 15B, 16A, and 16B. FIG. 15A is a schematic illustration of a real-time two-dimensional image of the lumen of the patient of FIG. 13, during visual maneuvering of the catheter of FIG. 13, toward a selected position within the lumen. FIG. 15B is a schematic illustration of a real-time three-dimensional image of the lumen, during automatic maneuvering of the catheter toward the selected position within the lumen. FIG. 16A is a schematic illustration of the lumen of FIG. 15A, when the medical device located at tip of the catheter, has reached the selected position. FIG. 16B is a schematic illustration of the lumen of FIG. 15B, when the medical device has reached the selected position.

With reference to FIG. 15A, a real-time superimposed two-dimensional image 760 of lumen 722 (FIG. 13) includes a real-time image of catheter 732, a real-time image of a medical device 762, and marks 808, 810, and 812. A front end and a rear end of the real-time image of medical device 762 in real-time superimposed two-dimensional image 760, is represented by lines 764 and 766, respectively.

With reference to FIG. 16A, the operator visually maneuvers catheter 732 within lumen 722. When lines 764 and 766 line up with marks 808 and 812, respectively, the operator is assured that medical device 762 is actually located at the selected position, and ready for performing the medical operation.

With reference to FIG. 15B, a real-time superimposed three-dimensional image 790 of lumen 722 includes a real-time image of catheter 732, a real-time image of medical device 762, and marks 792, 794, and 796. Since real-time superimposed three-dimensional image 790 is defined in the three-dimensional coordinate system, the position data of any point which the operator inputs to processor 666 is associated with three coordinates. Therefore, each of marks 792, 794, and 796 is associated with three coordinates in the three-dimensional coordinate system. A front end and a rear end of the real-time image of medical device 762 in real-time superimposed three-dimensional image 790, is represented by ellipses 798 and 800, respectively.

With reference to FIG. 16B, the operator visually maneuvers catheter 732 within lumen 722. When ellipses 798 and 800 line up with marks 792 and 796, respectively, the operator is assured that medical device 762 is actually located at the selected position, and ready for performing the medical operation. Alternatively, display 668 displays real-time superimposed three-dimensional image 790 as a stereoscopic image.

Figure 17:
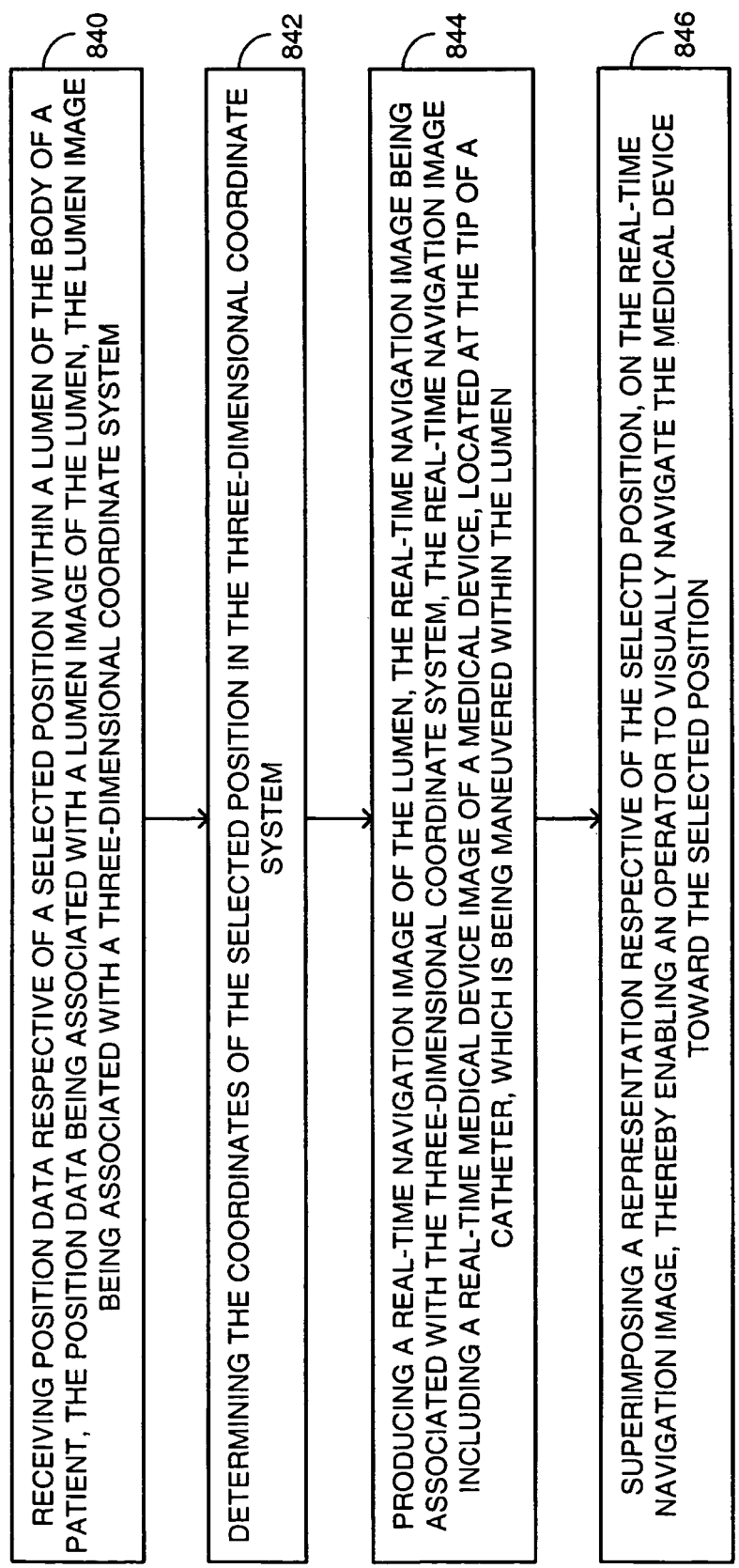
FIG. 17, which is a schematic illustration of a method for operating the system of FIG. 13, according to another embodiment of the disclosed technique.

Reference is now made to FIG. 17, which is a schematic illustration of a method for operating the system of FIG. 13, according to another embodiment of the disclosed technique. In procedure 840, position data respective of a selected position within a lumen of the body of a patient is received, the position data being associated with a lumen image of the lumen, the lumen image being associated with a three-dimensional coordinate system. With reference to FIGS. 13, 14A, the operator inputs position data respective of marks 726, 728, and 730 to processor 666, via user interface 664, by marking on image 720. With reference to FIGS. 13, 14B, the operator inputs position data respective of marks 802, 804, and 806 to processor 666, via user interface 664, by marking on image 724. Each of the marks 726, 728, 730, 802, 804, and 806 is associated with a set of two-dimensional coordinates.

In procedure 842, the coordinates of the selected position in the three-dimensional coordinate system, are determined. With reference to FIGS. 13, 14A, 14B, and 15A, processor 666 determines the coordinates of mark 808 according to the coordinates of marks 726 and 802, of mark 810 according to the coordinates of marks 728 and 804, and of mark 812 according to the coordinates of marks 730 and 806. Each of marks 808, 810, and 812 is associated with three coordinates.

Processor 666 produces a real-time navigation image of the lumen (procedure 844). The real-time navigation image is associated with the three-dimensional coordinate system, and includes a real-time medical device image of a medical device, located at the tip of a catheter, which is being maneuvered within the lumen.

In procedure 846, a representation respective of the selected position is superimposed on the real-time navigation image, thereby enabling an operator to visually navigate the medical device toward the selected position. With reference to FIGS. 13 and 15A, processor 666 produces real-time superimposed two-dimensional image 760, by superimposing a representation of each of marks 808, 810, and 812 on a real-time two-dimensional image of lumen 722, of catheter 732, and of medical device 762. Thus, the operator can visually navigate medical device 762 toward the selected position, according to real-time superimposed two-dimensional image 760.

According to another aspect of the disclosed technique, different trajectories of an MPS catheter within the lumen is determined, corresponding to different activity states of an organ of the patient, by moving the MPS catheter within the lumen. Each trajectory is defined in a three-dimensional MPS coordinate system, and is time-tagged with the corresponding activity state. Each trajectory is superimposed on a real-time two-dimensional image of the lumen, according to the activity state associated with the real-time two-dimensional image. This superimposed real-time two-dimensional which is associated with the organ timing signal detected by an organ timing signal monitor, is displayed on the display, thereby enabling the operator to mark the selected position on the superimposed real-time two-dimensional image. The operator, navigates the medical device to the selected position, either automatically or manually by employing the method of FIG. 5, as described herein above. Alternatively, the operator navigates the medical device to the selected position, visually, by employing the method of FIG. 17, as described herein above.

Figure 18:
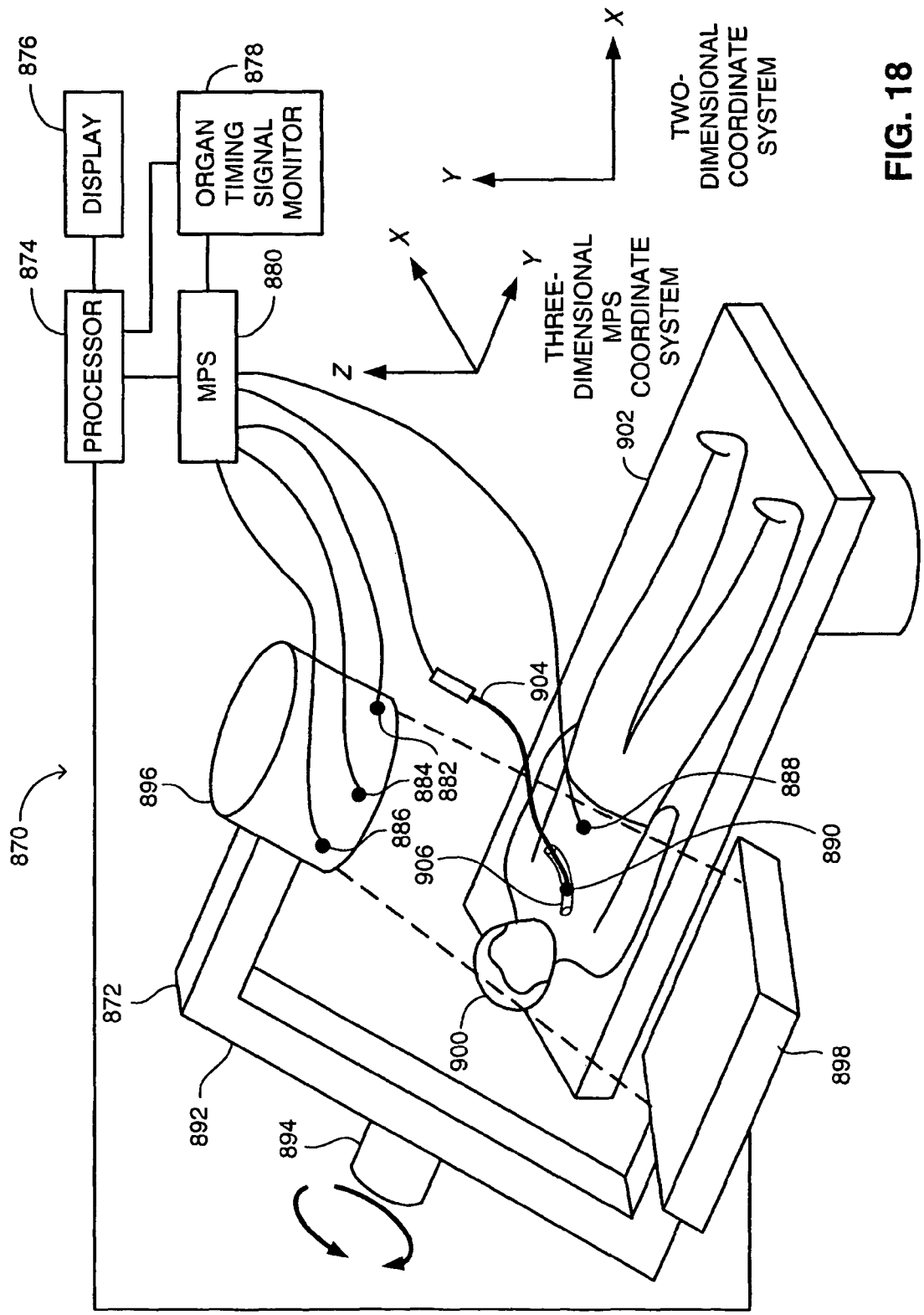
FIG. 18 is a schematic illustration of a system for producing a markable image, constructed and operative in accordance with a further embodiment of the disclosed technique.
Figure 19:
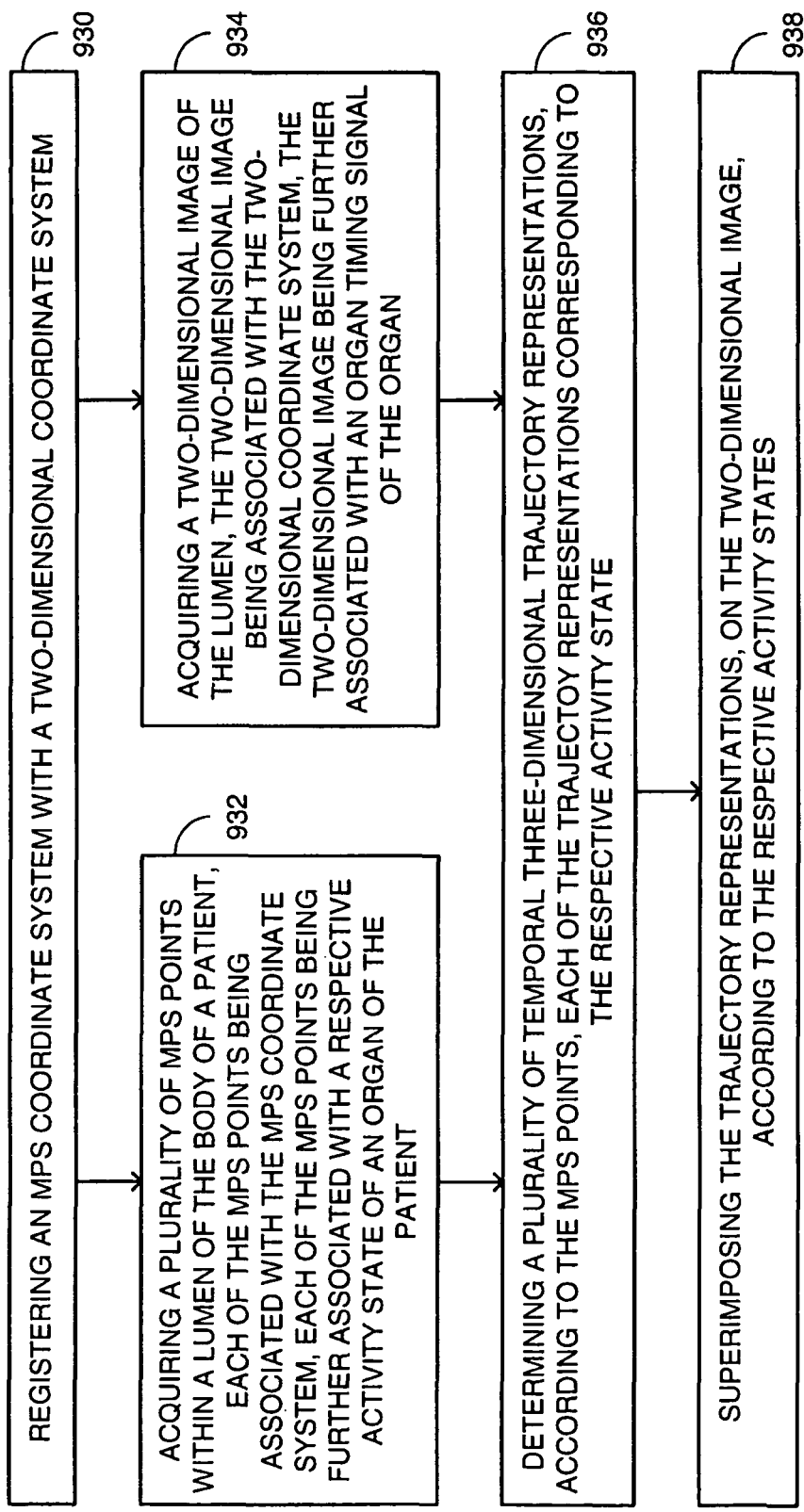
FIG. 19 is a schematic illustration of a method for operating the system of FIG. 18.
Figure 20:
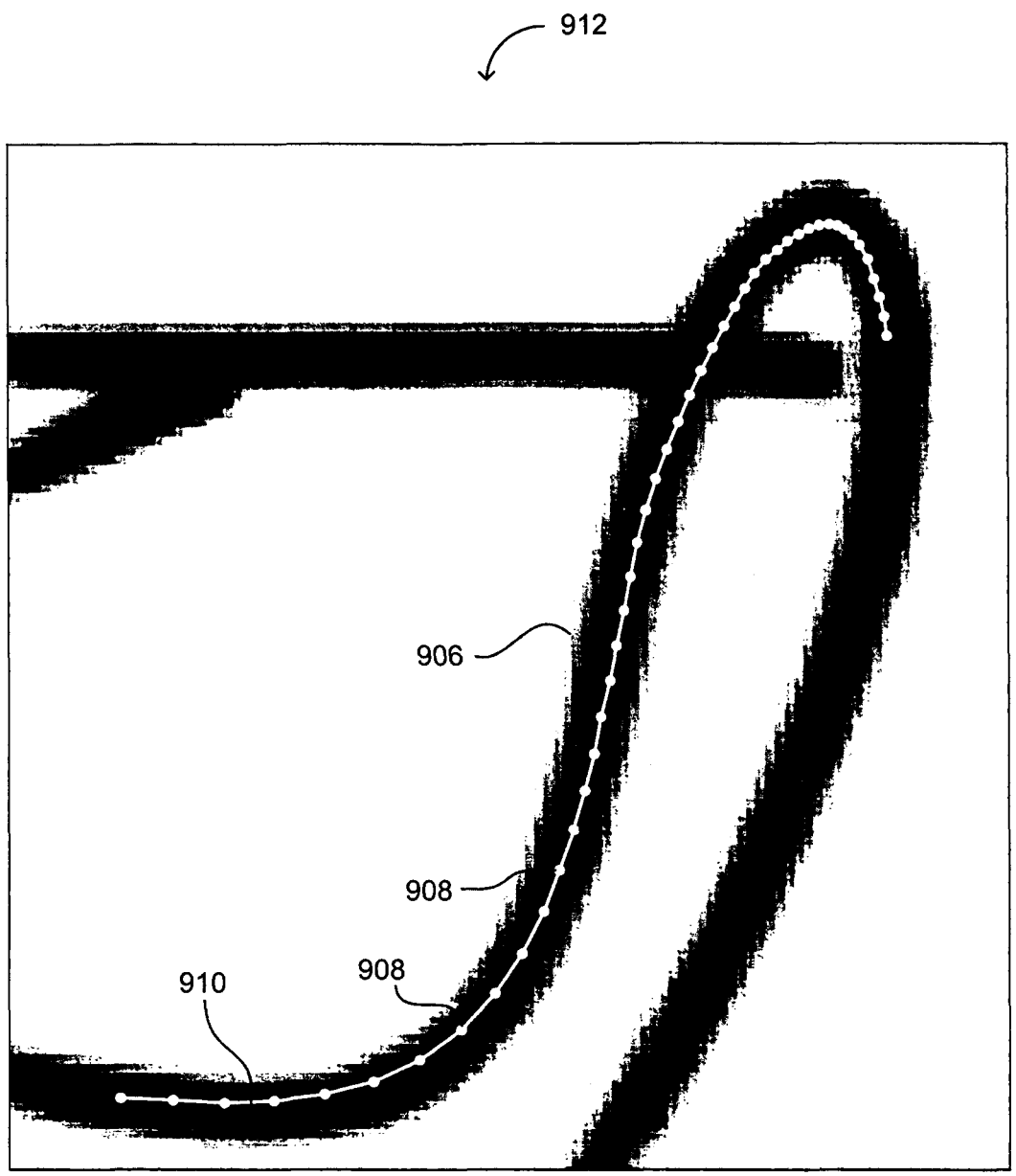
FIG. 20 is a schematic illustration of the markable image produced by the system of FIG. 18.

Reference is now made to FIGS. 18, 19, and 20. FIG. 18 is a schematic illustration of a system generally reference 870, for producing a markable image, constructed and operative in accordance with a further embodiment of the disclosed technique. FIG. 19 is a schematic illustration of a method for operating the system of FIG. 18. FIG. 20 is a schematic illustration of the markable image produced by the system of FIG. 18.

With reference to FIG. 18, system 870 includes an image acquisition device 872, a processor 874, a display 876, an organ timing signal monitor 878, an MPS 880, a plurality of transmitters 882, 884, and 886, and MPS sensors 888, and 890. Image acquisition device 872 includes a structural member 892, a moving mechanism 894, an emitter 896, and an image detector 898. Processor 874 is coupled with display 876, organ timing signal monitor 878, MPS 880, and with image detector 898. MPS 880 is coupled with transmitters 882, 884, and 886, and with MPS sensors 888, and 890. Moving mechanism 894, emitter 896, and image detector 898 are coupled with structural member 892. Image acquisition device 872 is similar to image acquisition device 662 (FIG. 13), as described herein above. Image acquisition device 872 is a two-dimensional image acquisition device, which is associated with a two-dimensional coordinate system.

Transmitters 882, 884, and 886 are firmly attached to emitter 896. Thus, the two-dimensional coordinate system of image acquisition device 872 is registered with a three-dimensional coordinate system of MPS 880. MPS sensor 888 is firmly attached to the body of a patient 900 who is lying on a bed 902. MPS sensor 890 is located at the tip of an MPS catheter 904. Each of MPS sensors 888, and 890 responds to electromagnetic radiations which transmitters 882, 884, and 886 emit. MPS 880 determines the position of the body of patient 900, and the position of the tip of MPS catheter 904, according to an output of MPS sensors 888 and 890, respectively.

With reference to FIG. 19, in procedure 930, an MPS coordinate system is registered with a two-dimensional coordinate system. With reference to FIG. 18, since transmitters 882, 884, and 886 are firmly attached to emitter 896, the two-dimensional coordinate system of image acquisition device 872 is registered with the three-dimensional MPS coordinate system of MPS 880.

In procedure 932, a plurality of MPS points within a lumen of the body of a patient are acquired, each of the MPS points being associated with the MPS coordinate system, each of the MPS points being further associated with a respective activity state of an organ of the patient. With reference to FIG. 18, as MPS catheter 904 moves within a lumen 906 of the body of patient 900, MPS 880 determines the respective position of the tip of MPS catheter 904, in the three-dimensional MPS coordinate system, at a plurality of MPS points 908 (FIG. 20) within lumen 906. Organ timing signal monitor 878 determines the activity states of an organ (not shown) of patient 900 (e.g., the heart). Processor 874 determines the three-dimensional coordinates of each of MPS points 908, according to position data received from MPS 880. Processor 874 associates the data received from organ timing signal monitor 878, respective of each activity state, with the respective sets of the three-dimensional coordinates, similar to the procedure described herein above in connection with FIG. 6B. MPS points 908 can be acquired either during a forward movement (i.e., threading) of MPS catheter 904 within lumen 906, or a backward movement therein (i.e., pull-back).

In procedure 934, a two-dimensional image of the lumen is acquired, the two-dimensional image being associated with the two-dimensional coordinate system, the two-dimensional image being further associated with an organ timing signal of the organ. With reference to FIG. 18, image acquisition device 872 acquires a two-dimensional image of lumen 906. This two-dimensional image can be either a still image, a sequence of images (i.e., cine-loop), or a real-time image. This two-dimensional image is defined in the two-dimensional coordinate system of image acquisition device 872. Processor 874 receives data respective of this two-dimensional image from image detector 898, and associates this data with an organ timing signal of the organ of patient 900. The organ timing signal includes data respective of different activity states of the organ. Processor 874 associates each activity state with the corresponding two-dimensional image.

In procedure 936, a plurality of temporal three-dimensional trajectory representations is determined, according to the MPS points, each of the trajectory representations corresponding to the respective activity state. With reference to FIGS. 18 and 20, processor 874 determines a trajectory representation similar to trajectory representation 910, corresponding to a respective activity state, by successively connecting those MPS points which correspond to that activity state. Processor 874 determines similar trajectory representations corresponding to other activity states, in a similar manner. Each trajectory representation is three-dimensional (i.e., in the sense of the three-dimensional MPS coordinate system), and corresponds to a specific activity state of the organ. Each trajectory representation can be determined for example, as described herein above in connection with FIG. 6B.

In procedure 940, the trajectory representations are superimposed on the two-dimensional image, according to the respective activity states. With reference to FIGS. 6A, 18 and 20, processor 874 superimposes each of the trajectory representations which was determined in procedure 938, on the two-dimensional image. For example, a two-dimensional image 912 (FIG. 20), corresponds to activity state $T_2$ (FIG. 6A), and trajectory representation 910 which also corresponds to activity state $T_2$, is superimposed on two-dimensional image 912.

Two-dimensional image 912 is a markable image, which the operator can employ for marking thereon, the selected position toward which the medical device is to be navigated to within lumen 906 (FIG. 18). The operator can designate the selected position according to procedure 160 (FIG. 5), as described herein above, via a user interface coupled with the processor. For this purpose, processor 874 superimposes an MPS representation respective of each of MPS points 908, on two-dimensional image 912, thereby enabling the operator to designate the selected position on two-dimensional image 912. The selected position is associated with one or more MPS representations. The operator can proceed to navigate the medical device within the lumen, toward the selected position, either manually or automatically, according to procedures 172 and 174. In case two-dimensional image 912 is a real-time image or a cine-loop, the operator can employ two-dimensional image 912 during the navigation.

Alternatively, the operator can designate the selected position toward which the medical device is to be navigated to, according to procedure 840 (FIG. 17). In this case, the operator can proceed to visually navigate the medical device toward the selected position, according to procedure 846.

When a three-dimensional representation of an object is projected on a two-dimensional image, the true dimensions of the object may be distorted. For example, a sphere will appear as a circle if projected onto a two-dimensional image plane. When the object is a lumen within the human body, such as a coronary artery, that lumen may curve "into" or "out of" the image plane. Thus, the true length of the lumen may be distorted. This phenomenon is called foreshortening. Since the three-dimensional representation of the lumen was constructed from a three-dimensional trajectory of a catheter, within the lumen, the system provides the operator with information regarding the true length of the displayed lumen. Furthermore, the system provides the operator with a representation of the true length of the lumen on the two-dimensional image.

With reference to FIG. 7, trajectory representation 910 of lumen 906 is superimposed on two-dimensional image 912. Additionally, MPS points 908, equally spaced on trajectory representation 910, are also superimposed on two-dimensional image 912. Therefore, the distance between adjacent pairs of MPS points 908, on the plane of two-dimensional image 912, is observed to decrease, where the foreshortening phenomenon worsens. Thus, the operator has both a quantitative assessment of the length of lumen 906, and a visual aid to assess foreshortening phenomenon on two-dimensional image 912. According to a further aspect of the disclosed technique, the MPS points are colored differently where the foreshortening phenomenon worsens.

It will be appreciated by persons skilled in the art that the disclosed technique is not limited to what has been particularly shown and described hereinabove. Rather the scope of the disclosed technique is defined only by the claims, which follow.

The invention claimed is:

1. Method for delivering a medical device coupled with a catheter, to a selected position within a lumen of the body of a patient, the method comprising the procedures of:
registering a three-dimensional coordinate system with a two-dimensional coordinate system, said three-dimensional coordinate system being associated with a medical positioning system (MPS), said two-dimensional coordinate system being associated with a two-dimensional image of said lumen, said two-dimensional image being further associated with an organ timing signal of an organ of said patient;
acquiring MPS data respective of a plurality of points within said lumen, each of said points being associated with said three-dimensional coordinate system, each of said points being further associated with a respective activity state of said organ;
determining a temporal three-dimensional trajectory representation for each said respective activity states from said acquired MPS data which is associated with said respective activity state; and
superimposing said temporal three-dimensional trajectory representations on said two-dimensional image, according to said respective activity state,
receiving position data respective of said selected position, by selecting at least one of said points along said temporal three-dimensional trajectory representation;
determining the coordinates of said selected position in said three-dimensional coordinate system, from said selected at least one point;
producing a real-time navigation image of said lumen, said real-time navigation image being associated with said three-dimensional coordinate system, said real-time navigation image including a real-time medical device image of a medical device, located at the tip of a catheter, which is being maneuvered within said lumen; and
superimposing a representation respective of said selected position, on said real-time navigation image, thereby enabling an operator to visually navigate said medical device toward said selected position.

2. The method according to claim 1, further comprising a procedure of acquiring said two-dimensional image, after performing said procedure of registering.

3. The method according to claim 1, wherein said procedure of acquiring is performed by said MPS, according to an output of an MPS sensor located at the tip of an MPS catheter moving within said lumen.

4. The method according to claim 1, wherein said two-dimensional image is a real-time image.

5. The method according to claim 1, wherein said two-dimensional image is a previously acquired cine-loop image.

6. The method according to claim 1, wherein said two-dimensional image is a previously acquired still image frame.

7. The method according to claim 1, further comprising a procedure of providing a quantitative assessment of the length of said lumen, to said operator.

8. The method according to claim 1, further comprising a preliminary procedure of acquiring said organ timing signal.

9. The method according to claim 8, wherein said procedure of acquiring said organ timing signal, is performed by an organ timing signal monitor.

10. The method according to claim 8, wherein said procedure of acquiring said organ timing signal comprises the procedures of:
measuring by an MPS sensor located at the tip of an MPS catheter moving within said lumen, the movements of said lumen due to an organ cycle of said organ; and
determining said real-time organ timing signal by said MPS.

11. System for delivering a medical device to a selected position within a lumen of the body of a patient, the medical device being attached to a medical device catheter, the system comprising:
a medical positioning system (MPS) for acquiring MPS data respective of a plurality of points within said lumen, according to an output of an MPS sensor located at the tip of an MPS catheter moving within said lumen, each of said MPS points being associated with a three-dimensional coordinate system, said three-dimensional coordinate system being associated with said MPS, each of said points being further associated with a respective activity state of an organ of said patient;
a user interface for receiving position data respective of said selected position, said position data being associated with at least one MPS representation, each of said at least one MPS representation being associated with a respective one of said points; and
a processor coupled with said user interface and with said MPS, said processor determining a plurality of temporal three-dimensional trajectory representations, according to said MPS data, each of said temporal three-dimensional trajectory representations corresponding to said respective activity state, said processor producing a superimposed image by superimposing said temporal three-dimensional trajectory representations on a two-dimensional image, according to respective activity states of said organ, said two-dimensional image being associated with a two-dimensional coordinate system, said two-dimensional image being further associated with an organ timing signal of said organ, said two-dimensional coordinate system being registered with said three-dimensional coordinate system, thereby enabling an operator to visually navigate said medical device toward said selected position, when said two dimensional image is a real-time image.

12. The system according to claim 11, wherein said two-dimensional image is a real-time image.

13. The system according to claim 11, wherein said two-dimensional image is a cine-loop image.

14. The system according to claim 11, wherein said two-dimensional image is a still image.

15. The system according to claim 11, further comprising a display coupled with said processor, said display displaying said superimposed image.

16. The system according to claim 11, further comprising an image acquisition device coupled with said processor, said image acquisition device acquiring said two-dimensional image.

17. The system according to claim 16, wherein said image acquisition device is an X-ray machine.

18. The system according to claim 16, wherein said image acquisition device is a C-arm.

19. The system according to claim 16, wherein said image acquisition device is a guided intra-vascular ultrasound.

20. The system according to claim 16, wherein said image acquisition device is an external ultrasound image detector.

21. The system according to claim 11, further comprising:
an image acquisition device coupled with said processor, said image acquisition device acquiring said two-dimensional image;
a radio-opaque marker attached to said medical device catheter in the vicinity of said medical device; and
a display coupled with said processor, said display displaying a marker image of said radio-opaque marker in said two-dimensional image.

22. The system according to claim 11, further comprising an organ timing signal monitor coupled with said processor and with the body of said patient, said organ timing signal monitor monitoring said organ timing signal, said processor determining said organ timing signal, according to an output of said organ timing signal monitor.

23. Method for delivering a medical device coupled with a catheter, to a selected position within a lumen of the body of a patient, the method comprising the procedures of:
registering a three-dimensional coordinate system with a two-dimensional coordinate system, said three-dimensional coordinate system being associated with a medical positioning system (MPS), said two-dimensional coordinate system being associated with a two-dimensional image of said lumen, said two-dimensional image being further associated with an organ timing signal of an organ of said patient;
acquiring MPS data respective of a plurality of points within said lumen, each of said points being associated with said three-dimensional coordinate system, each of said points being further associated with a respective activity state of said organ;
determining a temporal three-dimensional trajectory representation for each said respective activity states from said acquired MPS data which is associated with said respective activity state;
superimposing said temporal three-dimensional trajectory representations on said two-dimensional image, according to said respective activity state;
receiving position data respective of said selected position, by selecting at least one of said points along said temporal three-dimensional trajectory representation;
determining the coordinates of said selected position in said three-dimensional coordinate system, from said selected at least one point;
determining the current position of said medical device in said three-dimensional coordinate system, according to an output of an MPS sensor attached to said catheter in the vicinity of said medical device;
maneuvering said medical device through said lumen, toward said selected position, according to said current position relative to said selected position; and
producing a notification output when said current position substantially matches said selected position.

24. The method according to claim 23, further comprising a procedure of acquiring said two-dimensional image, after performing said procedure of registering.

25. The method according to claim 23, wherein said procedure of acquiring is performed by said MPS, according to an output of an MPS sensor located at the tip of an MPS catheter moving within said lumen.

26. The method according to claim 23, wherein said two-dimensional image is a real-time image.

27. The method according to claim 23, wherein said two-dimensional image is a previously acquired cine-loop image.

28. The method according to claim 23, wherein said two-dimensional image is a previously acquired still image frame.

29. The method according to claim 23, further comprising a procedure of providing a quantitative assessment of the length of said lumen, to said operator.

30. The method according to claim 23, further comprising a preliminary procedure to acquiring said organ timing signal.

31. The method according to claim 30, wherein said procedure of acquiring said organ timing signal, is performed by an organ timing signal monitor.

32. The method according to claim 30, wherein said procedure of acquiring said organ timing signal comprises the procedure of:
measuring by an MPS sensor located at the tip of an MPS catheter moving within said lumen, the movements of said lumen due to an organ cycle of said organ; and
determining said real-time organ timing signal by said MPS.

33. The method according to claim 23, wherein said procedure of maneuvering is performed manually.

34. The method according to claim 23, wherein said procedure of maneuvering is performed automatically.

35. The method according to claim 23, further comprising a procedure of increasing an amplitude of said notification output, when said current position approaches said selected position, and decreasing said amplitude, when said current position recedes from said selected position.

36. System for delivering a medical device to a selected position within a lumen of the body of a patient, the medical device being attached to a medical device catheter, the system comprising:
a medical positioning system (MPS) for acquiring MPS data respective of a plurality of points within said lumen, according to a first output of a first MPS sensor located at the tip of an MPS catheter moving within said lumen, each of said MPS points being associated with a three-dimensional coordinate system, said three-dimensional coordinate system being associated with said MPS, each of said points being further associated with a respective activity state of an organ of said patient, said MPS determining the current position of said medical device within said lumen, in said three-dimensional coordinate system, according to a second output of a second MPS sensor attached to said medical device catheter in the vicinity of said medical device;

a user interface for receiving position data respective of said selected position, said position data being associated with at lease one MPS representation, each of said at lease one MPS representation being associated with a respective one of said points; and a processor coupled with said user interface and with said MPS, said processor producing a superimposed image, by superimposing a plurality of MPS representations respective of said MPS data, on a two-dimensional image of said lumen, thereby enabling said user interface to receive said position data from an operator, said two-dimensional image being associated with a two-dimensional coordinate system, said two-dimensional image being further associated with an organ timing signal of said organ, said two-dimensional coordinate system being registered with said three-dimensional coordinate system, said processor determining the coordinates of said selected position in said three-dimensional coordinate system, according to said position data, said processor producing a notification output, when said processor determines that said current position substantially matches said selected position.

37. The system according to claim 36, wherein said processor determines a plurality of temporal three-dimensional trajectory representations, according to said MPS data, each of said temporal three-dimensional trajectory representations corresponding to said respective activity state, said processor further superimposing said temporal three-dimensional trajectory representations on said two-dimensional image, according to respective activity states of said organ.

38. The system according to claim 36, wherein said two-dimensional image is a real-time image.

39. The system according to claim 36, wherein said two-dimensional image is a cine-loop image.

40. The system according to claim 36, wherein said two-dimensional image is a still image.

41. The system according to claim 36, further comprising a display coupled with said processor, said display displaying said superimposed image.

42. The system according to claim 36, further comprising an image acquisition device coupled with said processor, said image acquisition device acquiring said two-dimensional image.

43. The system according to claim 42, wherein said image acquisition device is an X-ray machine.

44. The system according to claim 42, wherein said image acquisition device is a C-arm.

45. The system according to claim 42, wherein said image acquisition device is a guided intra-vascular ultrasound.

46. The system according to claim 42, wherein said image acquisition device is an external ultrasound image detector.

47. The system according to claim 36, further comprising an organ timing signal monitor coupled with said processor and with the body of said patient, said organ timing signal monitor monitoring said organ timing signal, said processor determining said organ timing signal, according to an output of said organ timing signal monitor.

* * * * *